United States Patent
Gascoyne et al.

(10) Patent No.: US 10,413,912 B2
(45) Date of Patent: Sep. 17, 2019

(54) PROGRAMMABLE FLUIDIC PROCESSORS

(71) Applicant: THE BOARD OF REGENTS OF THE UNIVERSITY OF TEXAS SYSTEM, Austin, TX (US)

(72) Inventors: Peter R. C. Gascoyne, Bellaire, TX (US); Jody Vykoukal, Houston, TX (US); Jon Schwartz, Sugar Land, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 317 days.

(21) Appl. No.: 14/635,293

(22) Filed: Mar. 2, 2015

(65) Prior Publication Data
US 2016/0030951 A1 Feb. 4, 2016

Related U.S. Application Data

(63) Continuation of application No. 11/140,499, filed on May 27, 2005, now Pat. No. 8,974,652.
(Continued)

(51) Int. Cl.
*B01F 13/00* (2006.01)
*B01F 3/08* (2006.01)
(Continued)

(52) U.S. Cl.
CPC ............ *B03C 5/026* (2013.01); *B01F 3/0815* (2013.01); *B01F 13/0003* (2013.01);
(Continued)

(58) Field of Classification Search
CPC ................ G01N 13/00; G01N 2013/00; B01L 2400/0427; B01L 3/502; B01L 3/50273;
(Continued)

(56) References Cited

U.S. PATENT DOCUMENTS

| 4,390,403 A | 6/1983 | Batchelder | 204/547 |
| 4,418,346 A | 11/1983 | Batchelder | 345/107 |

(Continued)

FOREIGN PATENT DOCUMENTS

| DE | 3931851 | 4/1991 |
| EP | 1185373 | 8/2004 |

(Continued)

OTHER PUBLICATIONS

Vykoukal et al., Langmuir, 2003, 19, 2425-2433 (Year: 2003).*
(Continued)

*Primary Examiner* — Gurpreet Kaur
(74) *Attorney, Agent, or Firm* — Norton Rose Fulbright US LLP

(57) ABSTRACT

Disclosed are apparatuses, systems, and methods for programmable fluidic processors. In one embodiment, the invention involves manipulating droplets across a reaction surface of the processor substantially contact-free of any surfaces. The reaction surface and the electrodes of the processor may include a coating repelling the droplets. Further, the present invention provides for a suitable suspending medium for repelling droplets away from fixed surfaces.

35 Claims, 14 Drawing Sheets

Related U.S. Application Data

(60) Provisional application No. 60/577,856, filed on Jun. 8, 2004, provisional application No. 60/575,305, filed on May 28, 2004.

(51) Int. Cl.
*B01L 3/00* (2006.01)
*B03C 5/02* (2006.01)
*B03C 5/00* (2006.01)
*B01L 3/02* (2006.01)
*G01N 35/10* (2006.01)

(52) U.S. Cl.
CPC ...... *B01F 13/0071* (2013.01); *B01F 13/0076* (2013.01); *B01L 3/50273* (2013.01); *B01L 3/502715* (2013.01); *B01L 3/502792* (2013.01); *B03C 5/005* (2013.01); *B01F 13/0084* (2013.01); *B01L 3/0268* (2013.01); *B01L 2200/06* (2013.01); *B01L 2200/0605* (2013.01); *B01L 2200/0673* (2013.01); *B01L 2200/12* (2013.01); *B01L 2200/14* (2013.01); *B01L 2200/143* (2013.01); *B01L 2300/0645* (2013.01); *B01L 2300/089* (2013.01); *B01L 2300/0816* (2013.01); *B01L 2300/0819* (2013.01); *B01L 2300/165* (2013.01); *B01L 2300/166* (2013.01); *B01L 2400/0424* (2013.01); *G01N 2035/1034* (2013.01)

(58) Field of Classification Search
CPC ......... B01L 3/502792; B01L 3/502715; B01L 2300/165; B01L 2300/0645; B01L 2300/0819; B01L 2300/0816; B01L 2300/089; B01L 2300/166; G02B 26/00655; B01F 13/0071; B01F 13/0076
See application file for complete search history.

(56) References Cited

U.S. PATENT DOCUMENTS

| | | | |
|---|---|---|---|
| 4,619,670 A | 10/1986 | Malcolm et al. | 96/27 |
| 4,789,803 A | 12/1988 | Jacobsen et al. | 310/309 |
| 4,887,721 A | 12/1989 | Martin et al. | 209/579 |
| 4,896,174 A | 1/1990 | Stearns | 347/120 |
| 4,908,112 A | 3/1990 | Pace | 210/198.2 |
| 5,006,749 A | 4/1991 | White | 310/323.03 |
| 5,100,627 A | 3/1992 | Buican et al. | 422/108 |
| 5,126,022 A | 6/1992 | Soane et al. | 204/458 |
| 5,180,480 A | 1/1993 | Manz | 204/644 |
| 5,250,263 A | 10/1993 | Manz | 422/81 |
| 5,284,471 A | 2/1994 | Sage, Jr. | 604/20 |
| 5,296,114 A | 3/1994 | Manz | 204/451 |
| 5,344,535 A | 9/1994 | Betts et al. | 204/547 |
| 5,364,744 A | 11/1994 | Buican et al. | 430/321 |
| 5,427,663 A | 6/1995 | Austin et al. | 204/549 |
| 5,454,472 A | 10/1995 | Benecke et al. | 203/127.1 |
| 5,489,506 A | 2/1996 | Crane | 435/2 |
| 5,532,129 A | 7/1996 | Heller | 435/6 |
| 5,565,322 A | 10/1996 | Heller | 435/6 |
| 5,569,367 A | 10/1996 | Betts et al. | 204/547 |
| 5,569,591 A | 10/1996 | Kell et al. | 435/29 |
| 5,580,435 A | 12/1996 | Kovacs | 204/603 |
| 5,582,701 A | 12/1996 | Geis et al. | 204/451 |
| 5,585,069 A | 12/1996 | Zanzucchi et al. | 422/100 |
| 5,603,351 A | 2/1997 | Cherukuri et al. | 137/597 |
| 5,605,662 A | 2/1997 | Heller et al. | 422/68.1 |
| 5,632,957 A | 5/1997 | Heller et al. | 422/68.1 |
| 5,653,859 A | 8/1997 | Parton et al. | 204/450 |
| 5,681,484 A | 10/1997 | Zanzucchi et al. | 216/2 |
| 5,683,569 A | 11/1997 | Chung et al. | 205/775 |
| 5,750,015 A | 5/1998 | Soane et al. | 204/454 |
| 5,795,457 A | 8/1998 | Pethig et al. | 204/547 |
| 5,814,200 A | 9/1998 | Pethig et al. | 204/547 |
| 5,849,486 A | 12/1998 | Heller et al. | 435/6 |
| 5,858,195 A | 1/1999 | Ramsey | 204/601 |
| 5,888,370 A | 3/1999 | Becker et al. | 204/643 |
| 5,948,328 A | 9/1999 | Fiedler et al. | 264/5 |
| 5,993,631 A | 11/1999 | Parton et al. | 204/547 |
| 5,993,632 A | 11/1999 | Becker et al. | 204/547 |
| 6,017,696 A | 1/2000 | Heller | 435/6 |
| 6,027,623 A | 2/2000 | Ohkawa | 204/450 |
| 6,051,380 A | 4/2000 | Sosnowski et al. | 435/6 |
| 6,068,818 A | 5/2000 | Ackley et al. | 422/50 |
| 6,071,394 A | 6/2000 | Cheng et al. | 204/547 |
| 6,084,503 A | 7/2000 | Ruile et al. | 340/10.1 |
| 6,099,803 A | 8/2000 | Ackley et al. | 422/68.1 |
| 6,113,768 A | 9/2000 | Fuhr et al. | 204/643 |
| 6,129,828 A | 10/2000 | Sheldon, III et al. | 204/518 |
| 6,149,789 A | 11/2000 | Benecke et al. | 204/547 |
| 6,156,181 A | 12/2000 | Parce et al. | 204/600 |
| 6,156,389 A * | 12/2000 | Brown | B01L 3/50 427/295 |
| 6,169,394 B1 | 2/2001 | Frazier et al. | 324/71.4 |
| 6,287,832 B1 | 9/2001 | Becker et al. | 435/173.9 |
| 6,294,063 B1 | 9/2001 | Becker et al. | 204/450 |
| 6,641,708 B1 | 11/2003 | Becker et al. | 204/547 |
| 6,703,819 B2 | 3/2004 | Gascoyne et al. | 324/71.4 |
| 6,749,736 B1 * | 6/2004 | Fuhr | B01L 3/502761 204/600 |
| 6,790,330 B2 | 9/2004 | Gascoyne et al. | 204/547 |
| 6,866,762 B2 | 3/2005 | Gascoyne et al. | 204/547 |
| 6,893,547 B2 | 5/2005 | Gascoyne et al. | 204/547 |
| 6,977,033 B2 | 12/2005 | Becker et al. | 204/450 |
| 7,033,473 B2 | 4/2006 | Gascoyne et al. | 204/547 |
| 7,105,081 B2 | 9/2006 | Gascoyne et al. | 204/547 |
| 2002/0036139 A1 | 3/2002 | Becker et al. | 204/450 |
| 2002/0043463 A1* | 4/2002 | Shenderov | B01L 3/502784 204/450 |
| 2002/0063060 A1 | 5/2002 | Gascoyne et al. | 204/471 |
| 2002/0121529 A1* | 9/2002 | Hoummady | B01J 19/0046 222/113 |
| 2003/0015428 A1 | 1/2003 | Becker et al. | 204/547 |
| 2003/0119057 A1 | 6/2003 | Gascoyne et al. | 435/7.1 |
| 2003/0121788 A1* | 7/2003 | Gascoyne | B01L 3/50273 204/547 |
| 2003/0164295 A1 | 9/2003 | Sterling | 204/450 |
| 2003/0170698 A1 | 9/2003 | Gascoyne et al. | 435/6 |
| 2003/0171325 A1 | 9/2003 | Gascoyne et al. | 514/44 |
| 2003/0173223 A1 | 9/2003 | Gascoyne et al. | 204/547 |
| 2003/0183525 A1* | 10/2003 | Elrod | B01F 5/0085 506/32 |
| 2003/0192780 A1* | 10/2003 | Ala-Kleme | G01N 21/66 204/291 |
| 2004/0011651 A1 | 1/2004 | Becker et al. | 204/547 |
| 2004/0136876 A1* | 7/2004 | Fouillet | B01F 13/0071 422/514 |
| 2004/0159546 A1* | 8/2004 | Zhang | B01L 3/502715 204/403.01 |
| 2004/0211659 A1* | 10/2004 | Velev | B01F 13/0071 204/164 |
| 2005/0072677 A1 | 4/2005 | Gascoyne et al. | 204/547 |
| 2006/0070879 A1 | 4/2006 | Becker et al. | 204/450 |

FOREIGN PATENT DOCUMENTS

| | | |
|---|---|---|
| EP | 0885055 | 4/2007 |
| WO | WO 97/20210 | 6/1997 |
| WO | WO 97/34689 | 9/1997 |
| WO | WO 98/04355 | 2/1998 |
| WO | WO 99/62622 | 12/1999 |
| WO | WO 00/47322 | 8/2000 |
| WO | WO 00/69565 | 11/2000 |
| WO | WO 01/05511 | 1/2001 |
| WO | WO 01/05512 | 1/2001 |
| WO | WO 01/05513 | 1/2001 |
| WO | WO 01/05514 | 1/2001 |

(56) References Cited

FOREIGN PATENT DOCUMENTS

| WO | WO 02/088702 | 11/2002 |
|---|---|---|
| WO | WO 03/014739 | 2/2003 |

OTHER PUBLICATIONS

Extended European Search Report in European Application No. EP16192349 dated Feb. 20, 2017.
"Platform technology may have broad applicability for facilitating preparation and analysis of DNA/RNA from mixed cell test samples," *Nature Biotech.*, Internet: www.nanogen.com, 1998.
Ajdari, "Pumping liquids using asymmetric electrode arrays," *Phys. Rev. E.*, 61:R45-R48, 2000.
Batchelder, "Dielectrophoretic manipulator," *Rev. Sci. Instrum.* 54:300-302, 1983.
Bone et al., "Dielectric Properties of Hydrated Proteins at 9.9 GHz," *J. Chem. Soc., Faraday Trans.* I, (73):1605-1611, 1977.
Chan et al., "Electrorotation of liposomes: verification of dielectric multi-shell model for cells," *Biochim. Biophys. Acta.*, 1349:182-196, 1997.
Cheng et al., "Preparation and hybridizaton analysis of DNA/RNA from E. coli on microfrabricated bioelectronic chips," *Nature Biotech.*, 16:541-546, 1998.
Cho et al., "Creating, Transporting, Cutting, and Merging Liquid Droplets by Electrowetting-Based Actuation for Digital Microfluidic Circuits," *J. MEMS*, 12:70-80, 2003.
Clarkson et al., "Effect of solution conditions on protein damage in foam," *Biochem Eng J.*, 4:107-114, 2000.
Daniel et al., "Fast Drop Movements Resulting from the Phase Change on a Gradient Surface," *Science*, 291:633-636, 2001.
Fiedler et al., "Dielectrophoretic sorting of particles and cells in a microsystem," *Anal. Chem*, 70:1909-1915, 1998.
Fluri et al., "Integrated capillary electrophoresis devices with an efficient postcolumn reactor in planar quartz and glass chips," *Anal Chem*, 68:4285-4290, 1996.
Fuhr et al., "Positioning and manipulation of cells and microparticles using miniaturized electric field traps and travelling waves," *Sensors and Materials*, 7:131-146, 1995.
Fukunaga et al., "Space Change Foliation at the Interface between a Charge Transport Layer and a Polyester Film," *IEEE Trans. Dielectrics and Electr. Insul.*, 5:276-280, 1998.
Gallardo et al., "Electrochemical Principles for Active Control of Liquids on Submillimeter Scales," *Science* 283:57-60, 1999.
Ganan-Calvo and Lopez-Herrera, "The coupling of capillary flow focusing and electrospray," *Bull. Am. Phys. Soc.*, 56th Annual Meeting of the Division of Fluid Dynamics, 2003 (Abstract No. AG.010).
Gascoyne and Pethig, "Experimental and Theoretical Aspects of Hydration Isothemis for Biomolecules," *J. Chem. Soc., Faraday Trans. I*, (76):171-180, 1977.
Gascoyne and Vykoukal, "Dielectrophoresis-Based Sample Handling in General-Purpose Programmable Diagnostic Instruments," *Proc. IEEE*, 92:22-42, 2004.
Gascoyne and Vykoukal, "Particle separation by dielectrophoresis," *Electrophoresis 2002*, 23:1973-1983, 2002.
Gau et al., "Liquid Morphologies on Structured Surfaces: From Microchannels to Microchips," *Science*, 283:46-499, 1999.
Genzer and Efimenko, "Creating Long-Lived Superhydrophobic Polymer Surfaces Through Mechanically Assembled Monolayers," *Science*, 290:2130-2133, 2000.
Harrison et al., "Micromachining a Miniaturized Capillary Electrophoresis-Based Chemical Analysis System on a Chip," *Science*, 261:895-897, 1993.
Helbo et al., "A micro-cavity fluidic dye laser," *J. Micromech. Microeng.*, 13:307-311, 2003.
Heyman, "Acoustophoresis Separtaion Method," *J. Acoustical Soc. Am.*, 94:1176-1177, 1993 (Abstract No. 43.35.Zc).
Ichimura et al., "Light-Drive Motion of Liquids on a Photoresponsive Surface," *Science*, 288:1624-1626, 2000.
Jones and Kallio, "Dielectrophoretic Levitation of Spheres and Shells," *J. Electrostat.*, 6:207-224, 1979.
Jones et al., "Dielectrophoretic liquid actuation and nandroplet formation," *J. Appl. Phys.*, 89:1441-1448, 2001.
Kataoka and Troian, "Patterning liquid flow on the microscopic scale," *Nature*, 402:794-797, 1999.
Ku et al., "Direct measurement of electrospray droplets in submicron diameter using a freezing method and a TEM image processing technique,"*J. Aerosol. Sci.*, 32:1459-1477, 2001.
LaFuma and Quéré, "Superhydrophobic states," *Nature Materials*, 2:457-460, 2003.
Latta, "Miniaturization, parallel processing come to lab devices," *The Scientist*, Internet: www.the-scientiest.library.upenn.edu, 11(18):1, 1997.
Lee and Kim, "Surface-Tension-Driven Microactuation Based on Continuous Electrowetting," *J. Microelectromech. Syst.*, 9:171-180, 2000.
Li and Harrison, "Transport, manipulation and reaction of biological cells on-chip using electrokinetic effects," *Anal Chem*, 69:1564-1568, 1997.
López-Herrera and Gañán-Calvo, "Finite Liquid Conductivity effects on the breakup of charged capillary jets," *Bull. Am. Phys. Soc.*, 53rd Annual Meeting of the Division of Fluid Dynamics, 2003 (Abstract No. GP.006).
Lopez-Herrera et al., "Experimental validation of one-dimensional models for the breakup of charged capillary jets," 54th Annual Meeting of the Division of Fluid Dynamics, 2001 (Abstract No. AA.003).
Malec et al., "Space Charge and Anomalous Discharge Currents in Crosslinked Polyethylene," *IEEE Trans . Elec. Ins.*, 3:64-69, 1996.
Milner et al., "Dielectrophoretic classification of bacteria using differential impedance measurements," *Electronics Letters*, 34:66-68, 1998.
Moesner and Higuchi, "Electrostatic devices for particle microhandling," *Industry Applications Conference*, 13th IAS Annual Meeting, Orlando, FL, Oct. 8-12, 1995.
Nishioka et al., "Micro manipulation of cells and DNA molecules," *J. Electrostatics*, 35:83-91, 1995.
Pollack et al., "Electrowetting-based actuation of liquid droplets for microfluidic applications," *Appl. Phys. Lett.*, 77:1725-1726, 2000.
Pollack et al., "Investigation of Electrowetting-Based Microfluidics for Real-Time PCR Applications," *Micro Total Analysis Systems 2003*, 2:619-622, 2003.
Prins et al., "Fluid Control in Multichanel Structures by Electrocapillary Pressure," *Science*, 291:277-280, 2001.
Sammarco and Burns, "Thermocapillary Pumping of Discrete Drops in Microfabricated Analysis Devices," *AIChE J.*, 45:350-366, 1999.
Schmalzing et al., "DNA typing in thirty seconds with a microfabricated devices," *Proc Natl Acad Sci USA*, 94:10273-10278, 1997.
Schwartz et al., "Droplet-based chemistry on a programmable micro-chip," *Lab Chip*, 4:11-17, 2004.
Schwarz, Electrical interactions of membrane active peptides at lipid/water interfaces, *Biophys. Chem.*, 58:67-73, 1996.
Srinivasan et al., "Clinical Diagnostics on Human Whole Blood, Plasma, Serum, Urine, Saliva, Sweat, and Tears on a Digital Microfluidic Platfoim," *Micro Total Analysis Systems 2003*, 2:1287-1290, 2003.
Stroock et al., "Patterning Electro-osmotic Flow with Patterned Surface Charge," *Phys. Rev. Lett.*, 84:3314-3317, 2000.
Su et al., "Identification of the location of protein fouling on ceramic membranes under dynamic filtration conditions," *J. Membrane Sci.*, 163:265-275, 1999.
Su et al., "The Adsorption of Lysozyme at the Silica-Water Interface: A Neutron Reflection Study," *J. Colloid Interface Sci.*, 203:419-429, 1998.
Su et al., "The Conformational Structure of Bovine Serum Albumin Layers Adsorbed at the Silica-Water Interface," *J Phys Chem. B.*, 102:8100-8108, 1998.
Torkkeli, "Droplet microfluidics on a planar surface," *VTT Publications 504*, VTT Technical Research Centre of Finland, 2003.
Van Oss et al., "Water, Treated as the Continuous Liquid in and around Cells," *Cell Mol. Biol. (Noisy-le-grand).*, 47:721-723, 2001.

(56) References Cited

OTHER PUBLICATIONS

Vogler, "Water and the acute biological response to surfaces," *J Biomater. Sci. Polym.*, 10:1015-1045, 1999.

Vykoukal et al., "A Programmable Diectrophoretic Fluid Processor for Droplet-Based Chemistry," *Micro Total Analysis Systems 2001*, Kluwer Academic Publishers, The Netherlands, 72-74, 2001.

Vykoukal et al., "Dielectrically Addressable Microspheres Engineered Using Self-Assembled Monolayers," *Langmuir*, 19:2425-2433, 2003.

Vykoukal et al., "Engineered Dielectric Microspheres for Use in Microsystems," *Micro Total Analysis Systems 2002*, 1:335-337, 2002.

Washizu, "Electrostatic actuation of liquid droplets for microreactor applications," *IEEE Transactions on Ind. Appl.*, 34:732-737, 1998.

Zeleny, "Instability of Electrified Liquid Surfaces," *J. Phys. Rev.*, 10:1-6, 1917.

Zeng and Korsmeyer, "Principles of droplet electrohydrodynamics for lab-on-a-chip," *Lab Chip*, 4:265-277, 2004.

\* cited by examiner

Top View

PROGRAMMABLE FLUIDIC PROCESSORS

CROSS-REFERENCE TO RELATED APPLICATIONS

The present application is a continuation of U.S. patent application Ser. No. 11/140,499, filed May 27, 2005 (now U.S. Pat. No. 8,974,652), which claims the benefit of priority to U.S. Provisional Patent Application Ser. No. 60/575,305 filed on May 28, 2004 and U.S. Provisional Patent Application Ser. No. 60/577,856 filed on Jun. 8, 2004, all of which are hereby incorporated by reference in their entirety.

STATEMENT AS TO RIGHTS TO INVENTIONS MADE UNDER FEDERALLY-SPONSORED RESEARCH AND DEVELOPMENT

Aspects of this invention were made with government support of the DARPA contracts to University of Texas M.D. Anderson Cancer Center; the U.S. Navy, grant number N66001-97-8608; and/or the Army Research Office, grant number DAAD19-00-1-0515. Accordingly, the government may have certain rights in this invention

BACKGROUND OF THE INVENTION

1. Field of the Invention

The present invention relates to the field of fluidic processing, more particularly, to methods and apparatuses for a substantially contact-free manipulation of droplets in a fluidic processor.

2. Description of Related Art

A programmable fluidic processor (PFP) performs chemical and biochemical assays and synthesis. However, surface fouling and sample carryover are major issues in all biological assay systems because reaction mixtures may contain proteins, lipids, fatty acids and other molecules. Proteins generally have low hydration energies in their surface hydration shell making them easy to precipitate and to associate with surfaces. Similarly, fatty acids and lipids accumulate at hydrophobic-hydrophilic interfaces. Indeed, the interface between a polar and a non-polar medium develops a region of modified polarity in which bio-molecules may partition and exhibit accumulation, insolubility, and/or denaturation. Whenever a biological reagent-containing droplet wets a surface, it is almost inevitable that some degree of surface contamination can occur. Furthermore, electrical fields modify the association of amphiphilic materials at hydrophobic-hydrophilic interfaces. If the surface is the interface between the droplet and its suspending medium, rather than with a fixed surface, then that suspending medium may be replaced periodically to ensure that contamination is swept from the droplet processor and does not accumulate.

In the case of protein-containing droplets making contact with fixed surfaces, wetting by droplets as they move across the surface can produce a trail of denatured protein, resembling snails' tracks, and each passing droplet may add new protein or pick up some deposited by previous droplets. It is difficult to clean such proteins from surfaces and, obviously, contamination of the fixed reaction surface can render the droplet processor unusable at some point in time either through disruption of operation by carry-over interference or through modification of the surface wetting characteristics causing droplets to stick. This would seem to be a fundamental problem for droplet manipulation methods that rely on surface contact effects.

This shortcoming of conventional methodologies are not intended to be exhaustive, but rather are among many that tend to impair the effectiveness of previously known techniques concerning droplet manipulation in a fluidic processor; however, those mentioned here are sufficient to demonstrate that methodology appearing in the art have not been altogether satisfactory and that a significant need exists for the techniques described and claimed in this disclosure.

SUMMARY OF THE INVENTION

Programmable embedded microfluidic systems that could enable automated chemical synthesis and analysis have the potential to revolutionize a wide range of applications in life research, clinical diagnostics, environmental detection, drug discovery, pharmaceutical and food production, water and waste quality management, and throughout the chemical industry. For these microfluidic systems to be applicable, the architecture should allow adaptation to any application by the provision of appropriate sample connections, reagents, and programming. This would enable the systems to operate analogously to digital microprocessors that can be adapted to meet diverse needs through appropriate data interfaces and software. As such, the design of a programmable microfluidic device needs to take into account issues not only of programmability but also of compatibility with a wide range of reagents, solvents, sample types, and products.

In one embodiment, the invention involves an apparatus including a suspending medium with a plurality of droplets. A reaction surface, where the plurality of droplets may be manipulated, provides an interaction site. At least one electrode is coupled to the reaction surface in which the at least one electrode includes an insulating coating for preventing contact between the droplets and the at least one electrode. A controller is coupled to the at least one electrode and provides a dielectrophoretic (DEP) force on the droplets.

In another embodiment, the invention involves an apparatus including a suspending medium with droplets. A fixed layer including a passivation layer and a droplet-repellent coating provides an interaction site for the droplets. A signal generator, coupled to the fixed layer, applies a signal to the fixed layer for manipulating droplets on the fixed layer.

In other embodiments, system including a semiconductor chip is provided. A reaction surface and an array of electrodes for droplet manipulation are coupled to the semiconductor chip. The reaction surface includes a droplet-repellent coating, such that when a controller, coupled to the array of electrodes, applies a phase of a signal to the electrode, the droplet travels substantially contact free across the reaction surface.

In another embodiment, the disclosure involves a method which provides a fluidic process including a fixed surface with a droplet-repellent coating. A droplet is injected onto the surface, where an inhomogeneous AC field provided to the fixed surface creates a DEP force on the droplet. The droplet is manipulated substantially contact-free across the fixed surface.

According to other embodiments, the invention involves a method for injecting a droplet onto a surface. The droplet is formed at a tip of an injector orifice where an acoustical disturbance is provided to separate the droplet from the tip of the injector onto the surface. The method also provides for manipulating the droplet across the surface.

As is known in the art, computer readable medium may include, without limitation, a computer file, a software package, a hard drive, a floppy, a FLASH device, a CD- ROM, a hole-punched card, an instrument, an ASIC, firmware, a "plug-in" for other software, web-based applications, RAM, ROM, or any other type of computer readable medium.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The figures are examples only. They do not limit the scope of the invention.

DESCRIPTION OF ILLUSTRATIVE EMBODIMENTS

The present disclosure provides programmable fluidic processors in which droplet injection and movement on a planar reaction surface is driven by dielectrophoresis (DEP) under software control. Due to the DEP force, which does not require physical contact between the droplet and any surface and depends only on the dielectric properties of the droplet, it provides the capacity for processing droplets composed of polar or non-polar media and allows for versatility across a wide spectrum of applications.

Figure 1:
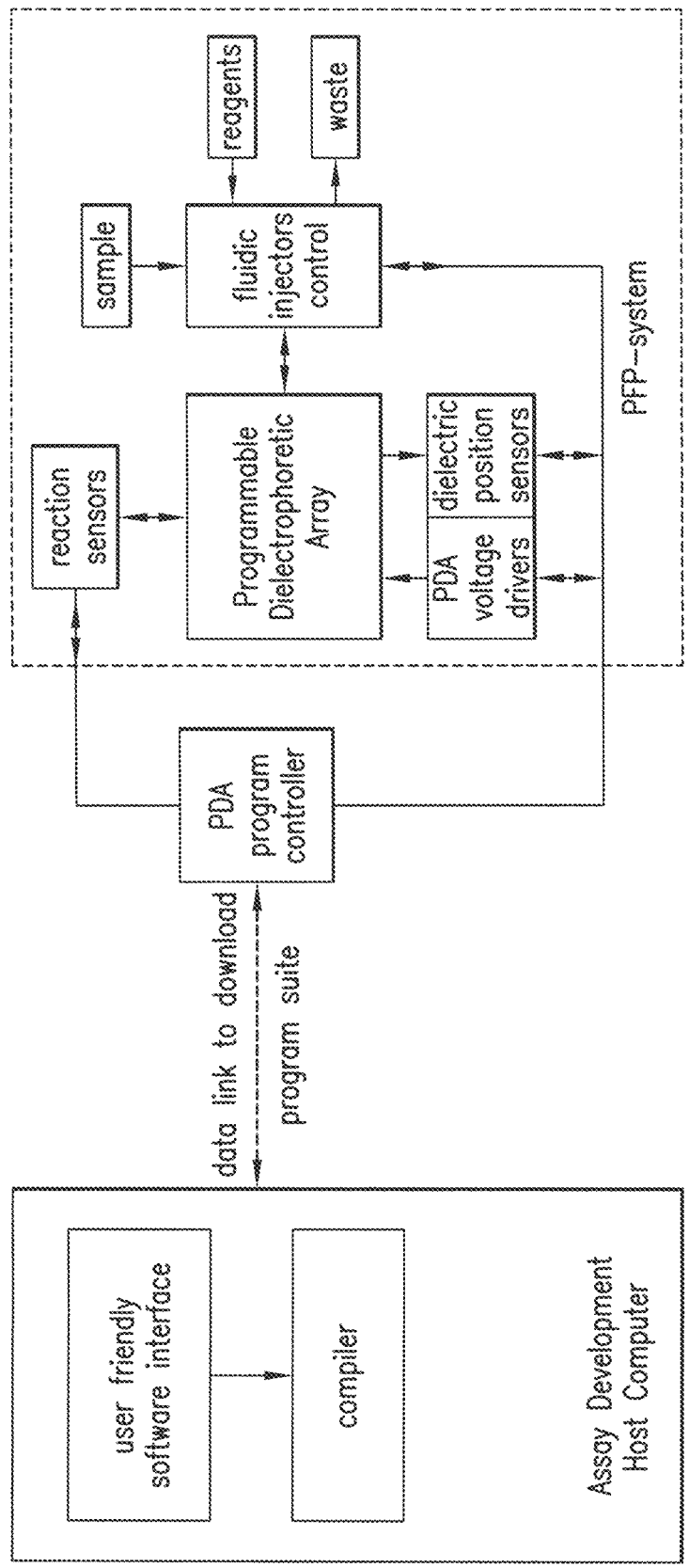
FIG. 1 shows a programmable fluidic processor (PFP) system, in accordance with embodiments of this disclosure.

In addition to discussing the application of DEP methods to the basic necessities of a droplet processor (namely droplet creation, metering, manipulation, and mixing), the present disclosure considers some of the practical requirements for versatility of programmable fluidic processors (PFP) systems including, for example, reliable operation in continuous processing applications. Contact-less droplet manipulation of droplet processor design can consider error detection, maintenance, and software issues. As an example of a DEP-based droplet processor, the present disclosure provides a complete operational DEP-based PFP system. This may employ a 1024-element droplet processor built on a scaleable CMOS architecture in which the switching electronics may be buried beneath the reaction surface and onto which the droplets may be injected and moved by DEP forces. The system may be controlled by a high level user interface equipped with a general-purpose droplet analysis programming package that includes error checking and the capability of driving any type of target droplet processor. A typical system organization plan for a programmable fluidic processor is shown in FIG. 1. For example, droplets of reagents and samples may be formed on the PFP-system and may be subsequently moved, merged, and measured under software control. The software for assays for the PFP system may be developed on separate simulation platform and downloaded or provided in ROM or any other storage medium.

DEP Theory

The origin of the DEP force is rather simple to understand in terms of system energy: the energy of an electric field is altered by the introduction of a dielectric body. If the electric field is inhomogeneous, the energy alteration may be greatest when the dielectric body is located in the region of highest field strength. The DEP force is simply the rate of change of electric energy with displacement of the dielectric body. For a spherical droplet of volume V in a stationary, inhomogeneous electric field E, the DEP force can be written as the spatial gradient of the electric energy $\Gamma$ as $$\vec{F}_{DEP} = \vec{\nabla}\,\Gamma = \frac{3}{2} V \varepsilon_s f_{CM} \vec{\nabla} E^2 \qquad \text{Eq. 1}$$

where $f_{CM}$ is the real part of the Claussius-Mossotti factor that describes the polarization of the droplet which is assumed to be suspended in a medium of dielectric constant $\varepsilon_s$. A DEP force exists in an inhomogeneous field even if the droplet has no contact at all with other matter and is located in a vacuum ($\varepsilon_s \to \varepsilon_0$, the permittivity of free space). This aspect represents the fundamental distinction between DEP (and the related phenomenon of optical trapping) and other forces that have been used to move droplets. All other phenomena explicitly depend on material contact to impose the forces that drag or push the droplets. For example, in the case of acoustophoresis, forces are provided by mechanical compression and, in the case of electrowetting-on-dielectric (EWOD) and thermocapillary pumping, forces are provided by differential wetting of a substrate on either side of the droplet.

Even though the imposition of DEP forces does not require contact with another material, all practical DEP-based droplet processors that have been developed so far nevertheless have surfaces with which droplets come into contact and, in addition, the droplets are usually suspended in an immiscible partitioning medium. A central challenge of DEP-based droplet processors, then, is how to prevent surface contamination and carry-over resulting from contact with samples and reagents. These issues will be discussed in detail later.

AC, rather than DC, fields are normally used to produce DEP forces, allowing the frequency-dependent permittivity of materials to be exploited and charge injection phenomena to be avoided. To understand how the properties of the droplet and its suspending medium affect the DEP force, it is helpful to examine more closely the Clausius-Mossotti polarization factor in Eq. 1. Under AC field conditions, the real component of the Clausius-Mossotti factor is given by $$f_{CM} = \text{Re}(f_{CM}^*) = \text{Re}\left(\frac{\varepsilon_d^* - \varepsilon_s^*}{\varepsilon_d^* + 2\varepsilon_s^*}\right) = \frac{(\varepsilon_d - \varepsilon_s)(\varepsilon_d + 2\varepsilon_s) + (\sigma_d - \sigma_s)(\sigma_d + \sigma_s)/\varpi^2}{(\varepsilon_d + 2\varepsilon_s)^2 + (\sigma_d + 2\sigma_s)^2/\omega^2} \quad \text{Eq. 2}$$

where $\varepsilon^*_d$ and $\varepsilon^*_s$ are the complex permitivities of the droplet and the suspending medium, respectively, that embody the real permittivity (i.e. the dielectric constant) and frequency dependent conductivities of the droplet and suspending medium materials as $\varepsilon^*_d = \varepsilon_d - j\sigma_d/\omega$ and $\varepsilon^*_s = \varepsilon_s - j\sigma_s/\omega$, where $\omega$ is the angular frequency of the applied electric field $j=\sqrt{1}$, and $\varepsilon$ and $\sigma$ are the respective permitivities and conductivities. It follows that both the permittivity and conductivity of the droplet and its suspending medium can influence the electric field energy and hence the DEP force.

Although it has been argued in the context of droplet processing that the frequency dependent conductivity "is not dielectrophoresis" and that only the real permittivity terms give rise to the DEP force, the majority of applications of DEP in the life sciences rely mainly on the conductivity-dependent Maxwell-Wagner polarization in which charge carriers accumulate at interfaces. A similar polarization process occurs in droplets due to the accumulation of charge carriers at the droplet surface and this effect gives rise to a "legitimate" DEP force component. An extreme example of conductivity-dependent polarization is illustrated by Batchelder's (1983) early experiments in which he moved metal ball bearings around by DEP forces. Those experiments also serve to demonstrate the ability of DEP to manipulate entirely non-wetting and non-deformable materials. Nevertheless, in typical droplet processing applications, the permittivity difference between aqueous droplets and a hydrocarbon suspending medium, for example, are so great as to insure that the permittivity, rather than the conductivity, terms dominate the DEP force at all frequencies.

Note that the real part of the Claussius-Mossotti factor, and hence the DEP force, in Eq. 2 can be positive (i.e. the droplet is pulled into the high field region and the suspending medium is displaced) or negative (i.e. the suspending medium is pulled into the high field region and the droplet is displaced), depending on the respective properties of the droplet and suspension medium. This offers two possibilities for droplet manipulation: dielectric trapping in which droplets are attracted to electrodes and "pulled" from place to place by DEP forces and dielectric caging in which droplets are confined and levitated in an electric field cage and "pushed" from place to place by DEP forces. Later, the results for both DEP attraction and DEP repulsion cases using the same droplet processor with polar and non-polar droplets, respectively, will be described in more detail.

The DEP forces may depend only on field-induced charge separation in the droplets; there is no requirement for droplets to carry a net charge as there would be for an electrophoretic force to be present. In one embodiment, AC fields are employed and net charges on droplets may not affect DEP manipulation. The defining feature of DEP, then, is that charge is not added to or removed from the droplets. This factor eliminates the requirement for droplets to touch a conductive surface to provide charge transfer as has to be used, for example, in EWOD.

While Eq. 1 is typically used to describe particle and cell trapping and sorting, there are significant practical differences in how it can be applied when considering droplet manipulation. In particle manipulation, the particles may usually be rigid and much smaller (5-10 times) than the electrodes and electrode gaps, and they only slightly perturb the applied electric field distribution. Under such circumstances, particle behavior can be predicted quite accurately by assuming that the field is not influenced by the particle and that the particle shape is not influenced by the field, allowing $\vec{\nabla}E^2$ to be defined by the electrode geometry alone and Eq. 1 to be solved directly. By contrast, in dielectrophoretic droplet manipulation, the droplets are often larger than the electrodes, electrode gaps, they are very close to the electrodes and significantly perturb the entire electric field distribution, and they are highly deformable in the field. Therefore, $\vec{\nabla}E^2$ is a function of droplet size, position, dielectric properties, and field induced deformation. Consequently, to understand and predict DEP-induced droplet manipulation, sophisticated modeling may be required.

Droplet Injection

Figure 2A:
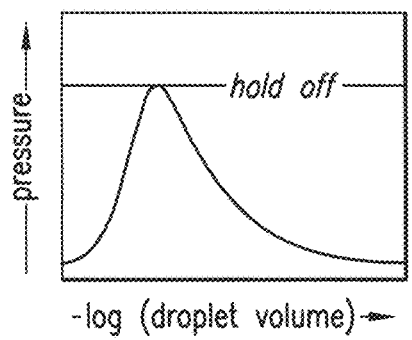
FIGS. 2A-2D show hydrostatic, interfacial, and dielectrophoretic forces used to control injections of droplets, in accordance with embodiments of this disclosure.
Figure 2B:
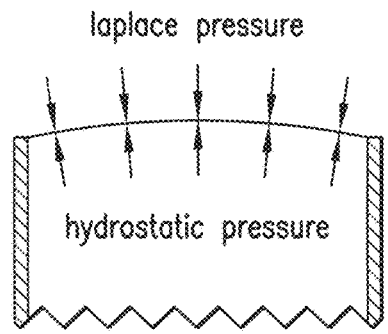
Figure 2C:
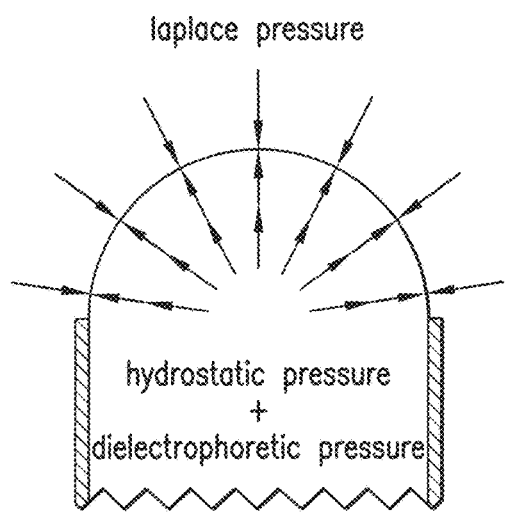
Figure 2D:
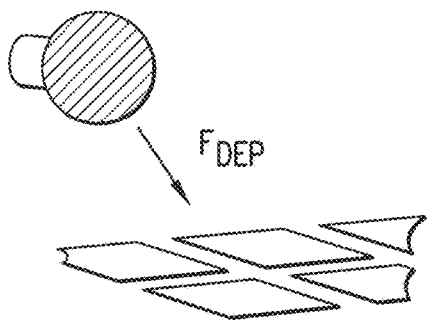

In one embodiment, a droplet processor may be used to create the droplets that can be manipulated on a reaction surface of the droplet processor. As such, the technique employed should be non-mechanical for reliability, and should also permit reactants to be drawn from adjacent reservoirs in a programmable manner in, for example, pico liter-scale aliquots so that larger droplets containing different, metered concentrations of reagents may be built on the reaction surface as required for various reactions or assays. Jones et al. (2001), Washizu (1998), Pollack et al. (2000), and Kim et al. (2003) have demonstrated droplet formation by electrode tracks that induce surface wetting. Generally the droplets are constrained to be of a single, relatively large volume, by this mechanism. The inventors have developed an alternative injection scheme (see FIGS. 2A-2D) based on the application of dielectric forces for building droplets from reservoirs adjacent to the reaction surface that allows for a wide range of droplet sizes, including very small droplets, to be produced. When the reservoir pressure is low, the fluid at an injector orifice may assume a flattened shape with a large radius of curvature, as seen in FIG. 2A. As the reservoir pressure is increased, a nascent aliquot of increasing volume, but decreasing sphere radius, may be formed. The internal pressure of the aliquot may reach a maximum when the radius of the droplet is equal to the radius of the injector orifice and the droplet is hemispherical in shape, as seen in FIG. 2B. Any further increase of the droplet volume may be associated with an increased droplet radius and correspondingly decreased internal pressure. In dielectrophoretic-injection, a hydrostatic pressure less than that required to overcome the hold-off may be applied to the fluid in the reservoir. The application of an AC electrical field between the droplet and a nearby electrode may provide a supplemental dielectrophoretic pressure that may overcome the hold-off condition, triggering droplet growth, as seen in FIG. 2C. The electrical field may also provide a lateral DEP force component that moves a droplet to a collection electrode once it has been released at a predetermined volume (FIG. 2D).

In one embodiment, a small-orifice injector may be located some distance from a much larger activation electrode. The fluid reservoir supplying the injector may be pressurized so that the fluid forms a convex interface at the orifice but below the point at which the capillary hold off $$\frac{2\gamma}{r}$$

pressure is exceeded and droplets form spontaneously from the orifice (γ is the interfacial surface tension of the droplet, r is its radius—see FIG. 2B). Fluid injection may be initiated by applying an AC voltage between the activation electrode and the fluid in the orifice. Because the orifice is very small, the electric field lines may converge at the orifice by the "lightning rod effect" and the local field at the orifice approximates $$E \approx \frac{V}{r} \quad \text{Eq. 3}$$

where V is the voltage applied between the activation electrode and the orifice. The incremental energy $\partial \Gamma$ stored in an incremental volume $\partial v$ of fluid flowing from the orifice into the nascent droplet is given by dielectric theory as $$\partial \Gamma = \frac{1}{2} E^2 \varepsilon_r f_{CM} \cdot \partial v \quad \text{Eq. 4}$$

so that the energy per unit volume in the electric field may be modified by the introduction of fluid into the orifice region by an amount $$\Pi \approx \frac{1}{2} \left( \frac{V}{r} \right)^2 \varepsilon_r f_{CM} \quad \text{Eq. 5}$$

This energy per unit volume represents a field-induced pressure that adds to the applied hydrostatic pressure. In one embodiment, for a 2 μm radius orifice, a 100 V applied AC voltage, water as the injected fluid, and bromododecane as the suspending medium filling the PFP, π is approximately 45 kPa, or about 50% of the hold-off pressure for an orifice of that size. If the hydrostatic pressure in the reservoir is sufficiently great, this field-induced pressure may be sufficient to overcome the capillary hold-off condition and initiate droplet formation, allowing the droplet to grow to a radius larger than that of the orifice. Once that occurs, the droplet may continue to fill from the reservoir because of hydrostatic pressure alone and the AC field may be removed if desired (see FIG. 2B).

It will be appreciated that in the case of a non-polar droplet being injected into a polar medium, the Clausius-Mossotti factor may be negative and the dielectric pressure component may act in a decremental fashion. In other words, when the field is applied, a nascent non-polar droplet may tend to be forced back into the injector orifice. In this case, the standing hydrostatic pressure in the injector can be adjusted to be greater than the hold-off pressure so that fluid may be injected in the absence of an applied AC field. The application of the field may then be used to impose a negative pressure component that prevents droplet formation, which may be initiated by the removal of the field. In the case of electrically non-conducting droplets, the electric field may be connected to a conductive orifice tip; by contrast, conductive fluids may be connected to the AC driving electronics by an electrode that is distal from the orifice and the fluid may participate in creating the conductive path to the droplet-formation region.

In addition to initiating fluid flow into the carrier medium, in order to form droplets on the fluidic processor reaction surface, the electrode configuration in the fluidic processor may provide a lateral DEP force component that may cause the nascent droplet to break off from the injector orifice and move to the collecting electrode when it has grown sufficiently. This effect is somewhat analogous to the formation of a water droplet at a dripping faucet—the growing droplet is generally released when the gravitational force on the nascent droplet exceeds the adhesion force between the droplet and faucet. The break-off of discrete droplets in such cases may be the result of interfacial instability triggered by the growth of an acoustical disturbance. In the DEP injection case, such a disturbance of the required wave-number may be generated by rapidly switching or pulsing the voltage applied to the activation electrode. In this way, droplet release can be explicitly triggered by a signal from the fluidic processor, allowing injected droplet sizes to be controllably modulated. Once a droplet separates from the orifice, its relaxation to a spherical shape imparts kinetic energy to it and it can fly off through the suspending medium, usually without touching the reaction surface, until it arrives at the collection electrode. This injection process may be actuated once or repeated rapidly. Droplet aliquots produced by multiple injection steps may spontaneously coalesce at the collecting electrode, allowing electronic control of the building of larger droplets and the addition of reagents to existing droplets brought from elsewhere in the processor.

Figure 13:
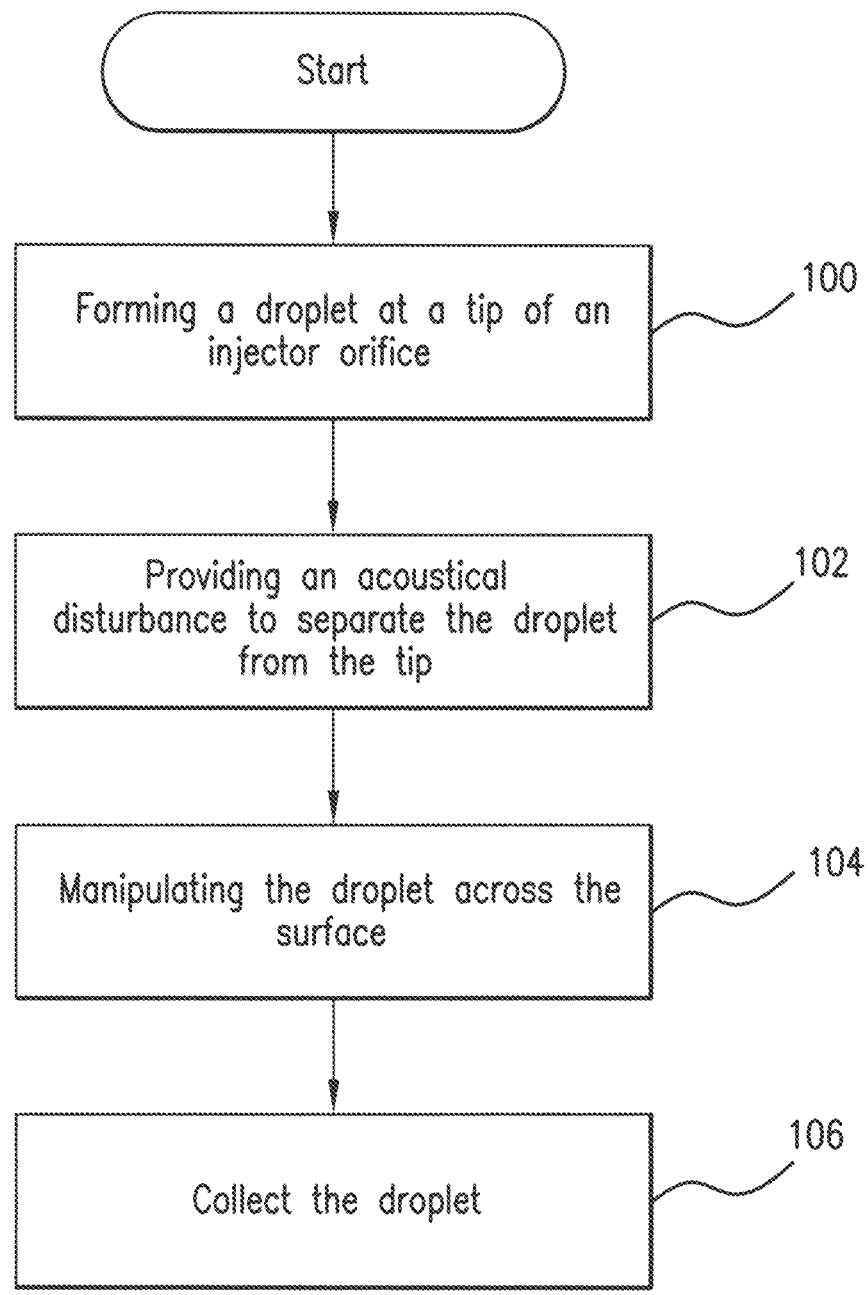
FIG. 13 is a flowchart showing steps of a method, in accordance with embodiments of this disclosure.

A flowchart showing steps for providing a droplet onto a surface according to embodiments of the present invention is given in FIG. 13. In step 100, a droplet is formed at a tip of an injector orifice. The droplet may be a hydrophobic or hydrophilic droplet. Alternatively, the droplet may be a polar or non-polar droplet. Upon forming a droplet of a predetermined volume or size, an acoustical disturbance, such as a lateral DEP force may be provided to separate the droplet from the tip, as shown in step 102. Alternatively, the acoustical disturbance may include switching or pulsing a voltage applied to one or more electrode coupled to a surface. The droplet may separate from the tip and onto a surface, where the droplet may be manipulated across the surface, as shown in step 104. In one embodiment, the surface may include a droplet-repellent coating such that as the droplet is manipulated across the surface, there is substantially no contact between the surface and the droplet. Further, the droplet may be suspending in a suspending medium, and thus, may allow for a substantially contact-free manipulation of the droplet across the surface. The droplet may subsequently be collected by a collecting electrode coupled to the surface, as shown in step 106.

In alternative embodiments, the acoustical disturbance of step 102 may be triggered by a signal from a controller such as a fluidic processor. The disturbance may cause the droplet to break away from the injector tip onto a surface of the fluidic processor, e.g., a reaction surface of the fluidic processor.

With this injection scheme, not only can the injection of aliquots be triggered by the application of an electric field but also aliquot volume may be controlled in, for example, in the 4 pL to 500 pL volume range by altering the field strength and droplet acoustical signals. Different injector-electrode geometries may be employed to obtain different injection characteristics. Two example designs are shown in FIGS. 3A-3D. The first of these is based on a drawn glass micropipette of the kind typically used in electrophysiology (FIG. 3A). By controlling the temperature and rate of capillary stretching, different orifice sizes may be achieved. The tips may be silanised or otherwise surface-treated as desired. The inventors have studied orifice diameters from 2 to 40 microns with this configuration. Droplets produced by this method do not touch the reaction surface until they arrive at the collection electrode. For example, referring to FIG. 3C, six aqueous droplets, viewed using a combination of epi-fluorescence and backlighting, have been formed on a reaction surface having an electrode pad array of 100 $\mu m \times 100$ $\mu m$. The two bright droplets have been injected with aliquots of a 5 mM fluorescein solution from the injector at the left. A 100 pl aliquot is shown in mid-flight as it is drawn from the micropipette-style injector toward a 4.2 nl droplet under the influence of an applied DEP force.

Figure 3B:
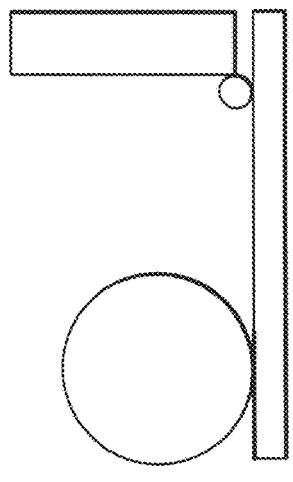
FIGS. 3A-3D show a side view (FIGS. 3A and 3B) and a top view (FIGS. 3C and 3D) for building droplets on a reaction surface by dielectrophoretic reagent metering, in accordance with embodiments of this disclosure.

The second design is a slot configuration that is fabricated within the wall of the PFP adjacent to the reaction surface (FIG. 3B). The inventors have experimented with slots from 4 to 7 microns in height and from about 2 to 10 microns in width fabricated in PDMS and are beginning experiments in silicon. In the slot design, droplets do touch the reaction surface during formation. For example, referring to FIG. 3D, a 7×10 $\mu m$ fluidic injector, molded into a PDMS wall of a reaction chamber is shown. The fluid injector is metering a 31 $\mu m$ diameter (15.6 pl) droplet of water into a larger 1.12 nl droplet located on a 100 $\mu m$ square electrode. The chamber wall appears as the dark vertical line at the right of FIG. 3D.

Once injected, droplets may be moved across to other injectors where additional aliquots of different reagents may be added to create droplets of desired composition. In this way, droplets of different volumes and containing different concentrations and mixtures of reagents may be constructed as needed for specific applications.

DEP droplet formation is entirely distinct from the so-called electrospray droplet formation phenomenon in which a pressurized fluid column flows from a small orifice into an extremely high DC electric field, is imparted with a net electrostatic charge by current flow, and flies apart into droplets as the result of instability caused by the electrostatic repulsion between the injected charges. The electrospray phenomenon is associated with extremely high electric fields, with the formation of a characteristic, convex "Taylor cone", and depends on charge injection. In the DEP method described here, the electric fields may be lower and may trigger fluid flow into the high field region. Furthermore, AC fields may be employed, charge does not need to be imparted onto the droplets, and the fluid surface remains convex at all times except briefly when an acoustic "jolt" destabilizes and releases each droplet from the orifice on demand.

Droplet Manipulation

Figure 4A:
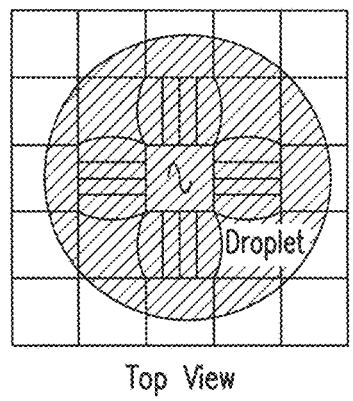
FIGS. 4A-4D show electrode excitation and fringing field patterns by dielectrophoresis on a PFP, in accordance with embodiments of this disclosure.
Figure 4B:
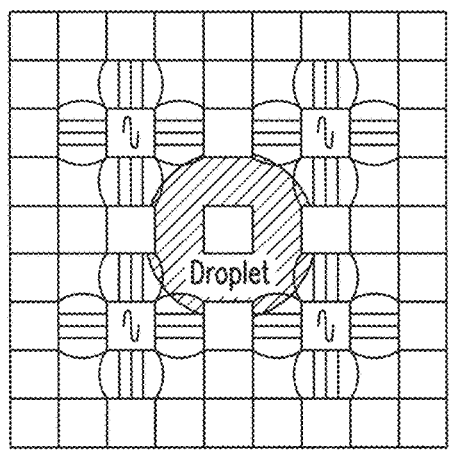
Figure 4C:
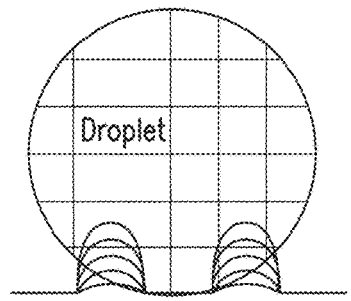
Figure 4D:
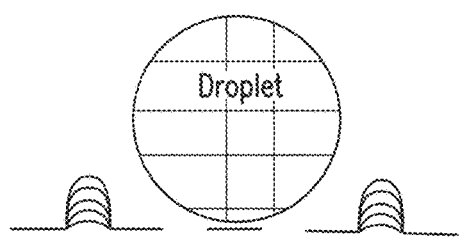
Figure 5B:
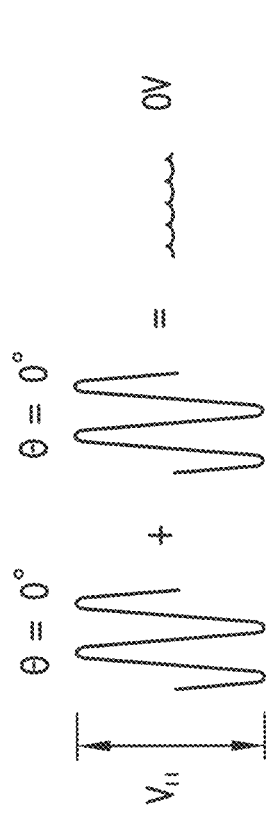
FIGS. 5A-5C show electrode excitation scheme in a PFP system, in accordance with embodiments of this disclosure.
Figure 5C:
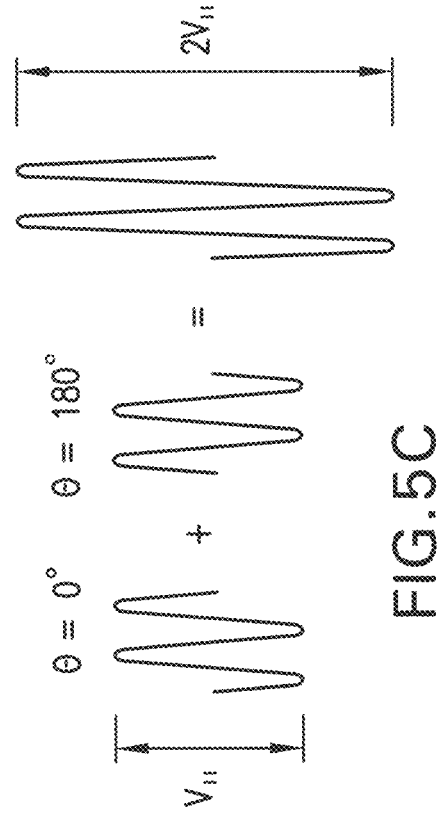
Figure 5A:
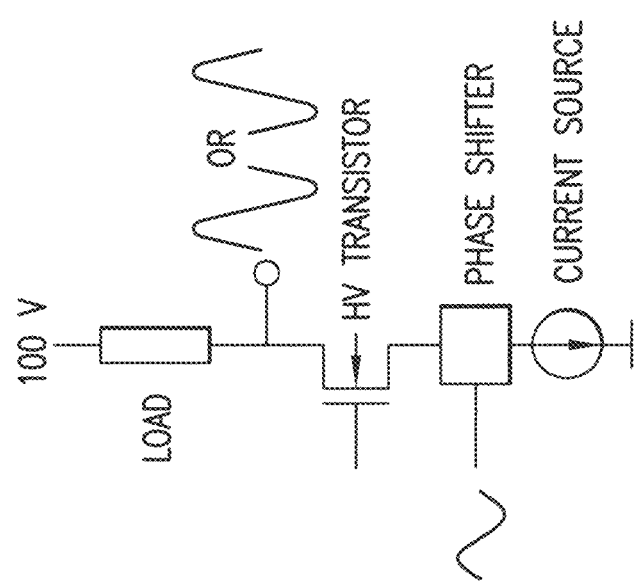

By appropriately energizing electrodes on the reaction surface, the electric field distribution may be reconfigured under electronic control and DEP forces (see Eq. 1) and may be imposed on droplets in order to transport them over the reaction surface. Referring to FIGS. 4A and 4B, which show the top and side views, respectively, for an excitation pattern for trapping droplets suspended in a non-polar partitioning medium. If, the Claussius-Mossotti factor is positive, droplets may be drawn by positive DEP forces towards the high field regions. In the case of non polar droplets in a polar medium, shown in FIGS. 4B and 4D, the electrodes can be energized so that the droplets are trapped inside potential energy "cages." In either case, by appropriately switching the excitation pattern of the electrode array, droplets may be translated from position to position. In one embodiment, a requirement for providing DEP forces is the electric field pattern, which may be provided by various excitation schemes. In the present disclosure, an AC signal may be imparted to all of the electrodes in the electrode array at all times. In one embodiment, a phase-shifting shift such as the one shown in FIG. 5A may be coupled to each electrode. If the signals are in phase, no field is developed between adjacent electrodes (FIG. 5B). To "energize" a specific electrode in this scheme, the phase of its excitation signal may be inverted relative to its neighbors, thereby creating a local AC field and corresponding DEP forces on any adjacent droplet (FIG. 5C).

By conducting this process simultaneously in many different locations on the electrode array, a whole ensemble of droplets may be translated along multiple, independent routes across the reaction surface. Sequentially applied switching configurations allow droplets to be transported to any desired locations and to be brought together for mixing when desired. Through appropriate combinations of activation steps, reaction schemes for the droplets may be accomplished alone or in parallel and only the number of electrodes in the array limits the number of droplets that may be handled simultaneously.

In one embodiment, if connections to the individual electrodes are run to the outside world along individual bus lines, a problem of scaling exists and there may be a practical limitation to the number of electrodes that can be placed on a surface. An alternative approach may be to use electronic addressing methods and signal switching electronics embedded at each electrode in the reaction surface. In this way, each electrode shares power buses but is independently addressable via X and Y coordinate addressing lines. Such an architecture may be scaleable to any required array size.

Figure 14:
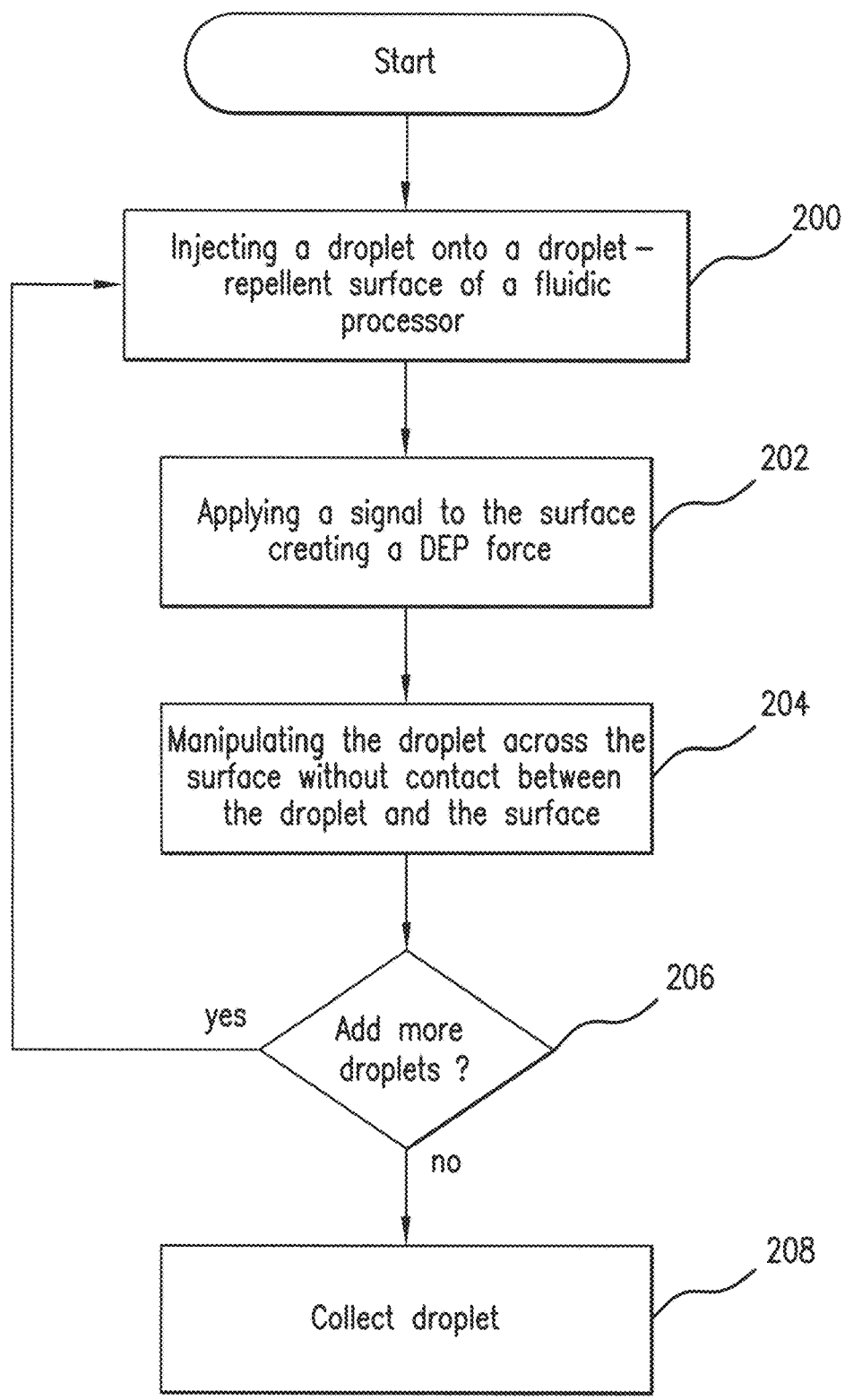
FIG. 14 is a flowchart showing steps of a method, in accordance with embodiments of this disclosure.

Referring to FIG. 14, a flowchart is provided showing steps for manipulating a droplet across a surface according to embodiments of the present disclosure. A droplet may be injected onto a fixed surface of a fluidic processor, as shown in step 200. In one embodiment, an acoustical disturbance may draw the droplet from an injector onto the fixed surface. The acoustical disturbance may be a lateral DEP force provided by the fluidic processor. Alternatively, the acoustical disturbance may be from switching or pulsing a voltage applied to activated electrodes of the fluidic processor.

In order to manipulate the droplet across the fixed surface, a signal such as an inhomogeneous AC field may be applied to the fixed surface creating a DEP force on the droplet, as shown in step 202. In one embodiment, the inhomogeneous AC filed may be applied to a plurality of electrodes of the fluidic processor. The DEP force on the droplet may cause the droplet to manipulate across the fixed surface. The fixed surface may include a droplet-repellent coating which may allow the droplet to manipulate across the fixed surface without contacting the surface, as shown in step 204. The substantially-contact free manipulation of droplets may allow for a reduction or even a complete elimination of contamination in the fluidic processor.

In one embodiment, fusing or mixing of droplets may be desirable. As such, decision box 206 of FIG. 14, allows for one or more droplets to be added to or mixed to the current droplet by repeating steps 200, 202, and 204 until the desired combination is concluded. After the mixing or fusing of the droplets is complete, the droplet may be collected by a collecting electrode of the fluidic processor, as shown in step 208. Alternatively, if no more droplets are desired, the current droplet may be manipulated and collected by a collection electrode (step 208).

Figure 15:
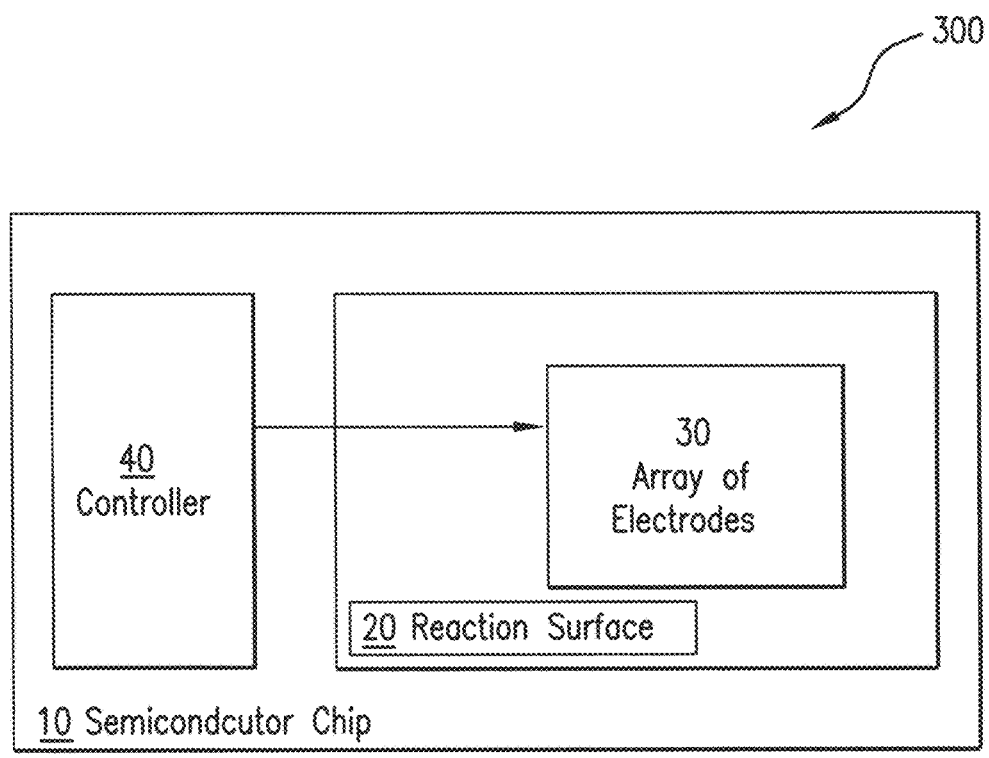
FIG. 15 is a block diagram of a system, in accordance with embodiments of this disclosure.

Referring to FIG. 15, a system 300 for manipulating droplet is shown. System 300 may include semiconductor chip, such as a CMOS chip 10, a reaction surface 20, an array of electrodes 30 coupled to the reaction surface, and a controller 40 coupled to the array of electrodes 30. In accordance to embodiments of the invention, the reaction surface 20 may include a droplet-repellent coating (approximately 1-5 micrometer layer) which may allow for the reduction or complete elimination of surface-droplet contact for reducing or even substantially eliminate cross-contamination between droplets as the droplets are manipulated through the system. Accordingly, the reaction surface 20 may include a layer of silicon dioxide or SU-8. In addition, the array of electrodes 30 may also include an insulating coating, which may reduce or eliminate contact between the droplets and electrodes. In one embodiment, the insulating coating may include $SiO_2$ or SU-8. Alternatively, the insulating coating may include spin-coated/baked TEFLON or sputtered TEFLON, metal oxide or thin-film dielectric, epoxy, siloxane, fluoropolymer, or any combination of the above. The insulating coating, in one example, may be chosen to prevent electrical current from passing between the electrode(s) and the droplets on the reaction surface.

A phase of a signal may be applied to at least one of the electrode by controller 40, dependent on the trajectory of the droplet across the reaction surface 20. In one embodiment, the signal may be an inhomogeneous AC signal which may generate a DEP force on the droplet suspending within a suspending medium. The suspending medium may also attribute to the contact free manipulation of the droplet on the reaction surface. In one embodiment, the suspending medium may provide buoyancy which may substantially eliminate sedimentation forces between the electrodes and the droplet. Further, the characteristics of the suspending medium may also reduce the affinity of the droplet to the electrodes, e.g., minimize or reduce interfacial tension between the droplet and the reaction surface. For example, for an aqueous droplet, the suspending medium may be a hydrophobic suspending medium. Alternatively, for a hydrophobic droplet, the suspending medium may include a hydrophilic medium such as water, DMF, ethanol, acetone, methanol, 1-bromodecane, and DMSO.

Droplet Volume

Because DEP may be a bulk effect that does not require the droplets to be flattened by a top surface, the top of the chamber can be high and droplets of widely ranging diameters may be manipulated. In the devices, spherical droplets in the range of about 20 to 100 micron diameter size can be injected dielectrically, allowing reagents and samples to be dispensed, for example, in 4 pL to 500 pL aliquots (a relative volume range spanning over two orders of magnitude). Alternatively, in other embodiments, droplets in the 50 to 600 micron size range (volumes from 65 pL to 110 nL and a relative volume range of 1:1700) can be transported (the maximum diameter is limited by the height of the chamber). Therefore, the concentration quantization steps in reagent titrations when injecting small droplets into larger ones can be as small as 1:27,000 and as large as 8:1.

An interesting compensatory aspect of the droplet radius-dependent geometry, field geometry, and Stoke's drag is that the speed at which droplets move from electrode to electrode does not alter significantly with droplet size. These features lend flexibility to the DEP-manipulation of samples, reagents, and composite droplets. Electrocapillary and EWOD methods sandwich the droplets between surfaces, so that droplet volume scales with (diameter)$^2$ rather than with (diameter)$^3$ as in the spherical droplet case used for DEP.

Droplet Suspending Media

As already indicated, the DEP force does not depend on surface interactions, but all practical DEP droplet processors that have been developed so far have surfaces with which droplets come into contact. These surfaces are of two types, namely (1) the interfacial surface between the droplets and the optional fluid medium in which they are suspended, and (2) the fixed surface(s) within which are arrayed the electrodes that produce the electric field configurations that provide the DEP forces. If DEP cages are being used to confine droplets, then the DEP force is repulsive and the droplets do not touch the fixed surface. In this case, the surface interaction is limited to the droplet-suspending medium interface.

In principle, the suspending medium is arbitrary, but in practice it serves three useful functions. First, it increases the DEP force, which, as revealed by Eq. 1, scales with the permittivity of the medium. Second, it provides buoyancy to the droplets, decreasing or eliminating sedimentation forces that can press droplets against the reaction surface and increase wetting. Third, it serves to prevent the transfer of droplet fluid or contents from one droplet to another via the vapor phase, which can occur if droplets of different diameter are being manipulated simultaneously on a droplet processor. This occurs because the thermodynamic potential of a droplet rises as its radius falls. As a result, small droplets tend to vaporize and the vapor may tend to migrate to, and condense in, larger droplets. By partitioning the droplets, the suspending medium prevents such vapor-phase transfer.

Other important characteristic of the suspending medium are that it should not dissolve reagents from the droplet and it should be of low viscosity to that droplets can move through it quickly without a large Stokes drag. Obviously it is also critical that the droplets and suspending medium be immiscible. While there are various physico-chemical aspects that affect miscibility and solubility, a useful one in the context is based on the Clausius-Mossotti factor in Eq. 2, which indicates the differences in polarisability of the droplet and its suspending medium and hence the respective "polarities" of their fluids. Generally, if $f_{CM}>0.75$ then immiscibility is assured for polar droplets in a non-polar suspending medium and if $f_{CM}<-0.38$ then immiscibility is assured for non-polar droplets in a polar suspending medium. These conditions are satisfied if the permittivity of one fluid is at least ten times that of the other and this state of affairs also assures strong DEP forces. Generally, then, if the fluids are chosen for good immiscibility they may give rise to strong DEP forces and vice-versa.

In one embodiment, pure 1-bromododecane, (density=1.04; viscosity=3.6 cP; permittivity=4.1 $\varepsilon_0$) may be used as a suspending media. The extent to which different reagents can partition from the droplets into 1-bromododecane may depend on their physical properties but the inventors have yet to encounter any case where contamination of the 1-bromododecane has been an issue. Nevertheless, the droplet processors are equipped with maintenance ports that allow the suspending medium to be replaced periodically should this become necessary or desirable.

Surface Issues

Even though the DEP force does not require surface contact, in practical DEP-based droplet processors droplets do usually make contact with surfaces and/or a suspending medium. When the droplet manipulation approach is droplet trapping, or positive DEP in which the droplets are pulled by positive DEP forces, there is, in addition to the medium interface, at least minimal contact between the droplets and the fixed surface within which the electrodes are embedded. This is unavoidable in the DEP trapping mode because droplets are drawn to the highest field regions at the electrode edges. To avoid undesired interactions, it may be necessary to passivate the electrodes with an insulating coating that prevents electrical current from flowing to the droplets or the suspending medium. This is especially important for large aqueous droplets and for polar suspending media that are electrically conductive since these could short circuit neighboring electrodes in the array. In one embodiment, a layer of between 1 and 5 microns, or upwards of 10 microns or more, may include metal oxide, epoxy, siloxane, fluoropolymer, photoresist, SiO2, SU-8, PDMS, Parylene, barium strontium titinate, a combination of any of the above, any thin-film dielectric, or some other dielectric material may be used for passivation. Alternatively, spin-coated/baked TEFLON, sputtered TEFLON, and diamond-like carbon as passivation layers have been used. In one embodiment, the thickness of the layer needs to be sufficient enough to prevent electrical current from passing across the passivation layer. In the CMOS droplet processor presented here, SiO2 was used as the passivation layer because this was a convenient option provided during chip fabrication. This passivation layer was covered by an additional dielectric spacer layer of 1 to 4 micron SU-8, as explained later.

The minimization of contact and avoidance of wetting of fixed surfaces may be important in droplet processor design if the processors are to be operated as embedded systems that can function for extended periods of time without carryover and contamination issues were considered. To minimize the area of droplet contact with the fixed surface in which the electrodes are embedded, appropriate droplet-repellent coatings on top of the passivation layer are used. According to embodiments of the present invention, if the droplets are aqueous then the suspending medium and the coatings of the fixed surfaces may be chosen to be hydrophobic. Conversely, hydrophilic coatings (such as, but not limited to, polylysine, PEG, or carboxylated agents), and suspending media (such as, but not limited to, water, DMF, ethanol, acetone, methanol, or DMSO) may be chosen when using hydrophobic droplets. Thus the present inventors have successfully manipulated water droplets in 1-bromodecane and silicon oil; DMF droplets in silicon oil; and 1-bromodecane or silicon oil droplets in water and DMF.

In one embodiment, minimizing surface interactions may be overcome by the use of micro-roughening or patterned micro-features on the fixed surfaces. In the case of aqueous droplets, this gives rise to a phenomenon known as superhydrophobicity in which the droplets are essentially supported on the tips of tiny hydrophobic "fingers", greatly reducing the contact area with the surface.

So that droplets prefer to remain in the suspending medium rather than attaching themselves to the fixed surfaces, it is also desirable that the droplets have less affinity for the fixed surfaces than for the suspending medium. This can be accomplished by making the surfaces more droplet-repellent than the suspending medium through appropriate choice of material polarities. For example, a material such as PTFE (permittivity=$2\varepsilon_0$) may be used to coat surfaces while a slightly more polar suspending medium such as 1-bromododecane (permittivity=$4\varepsilon_0$) may be employed when aqueous droplets are being used. For example, the interfacial energy of water and 1-bromododecane is less than that between water and PTFE, encouraging the droplets to remain in the suspending medium. Converse considerations may be applied for hydrophobic droplets. In according to embodiments of the present disclosure, the suspending medium may be chosen to provide buoyancy so that contact between the fixed surface and the droplets is minimized by lessening or eliminating sedimentation forces. In the processors, contact angles between droplets and the reaction surface approaching 180 degrees (corresponding to almost no wetting at all) for aqueous droplets suspended in 1-bromododecane on a perfluoro resin/vinyl micro-bead treated superhydrophobic reaction surface have been observed.

A surface phenomenon that can represent a caveat for DEP manipulation is charge injection, which, as already indicated, is required for EWOD but not for DEP transport of droplets. Droplets may begin to show electrowetting, and tend to "stick" to the reaction surface, when conditions of high voltages (~100V), low field frequencies (<1000 Hz), and long standing times (droplets completely stationary over an energized electrode for >1000 seconds) are employed simultaneously. Droplets that have "stuck" in this way may vibrate laterally in response to, and in phase with, a 5 Hz AC field, showing that they have become electrically charged. Since this occurs in the absence of contact with a conductor, this effect may result a net charge injection into the droplets from the reaction surface. In one embodiment, although the charge injection process, with frequency >2000 Hz and voltage <40 V are not completely understood, with the usual operating conditions, this problem is averted and droplets do not slowly build up charge or show any tendency to stick. The use of a superhydrophobic surface may reduce this charge injection effect also, by lessening the contact between the charge-injecting surface and the droplets. Charge injection has long been recognized as a problem in thin dielectric layers subjected to high DC electric fields and is obviously worthy of additional studies in the context of droplet processors.

Figure 6A:
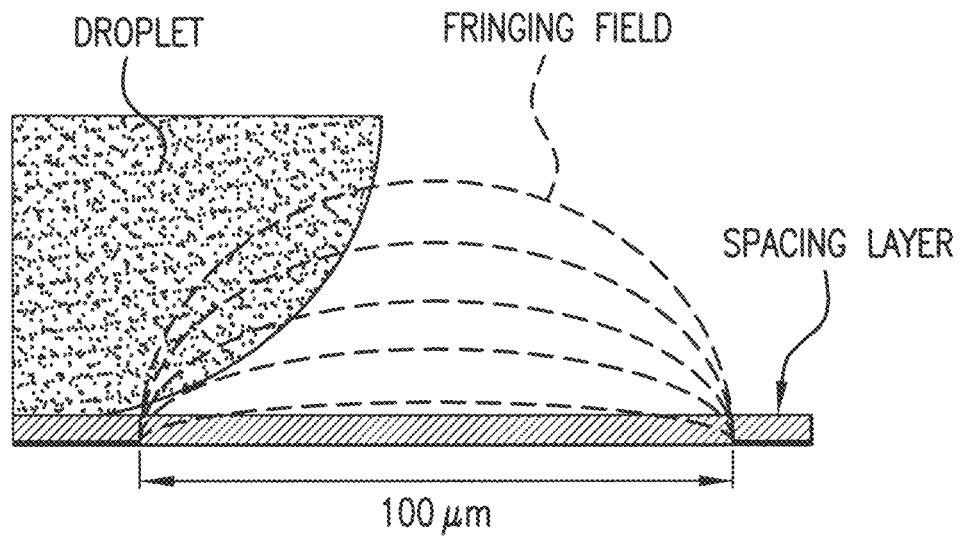
FIGS. 6A and 6B show field fringing lines, in accordance with embodiments of this disclosure.
Figure 6B:
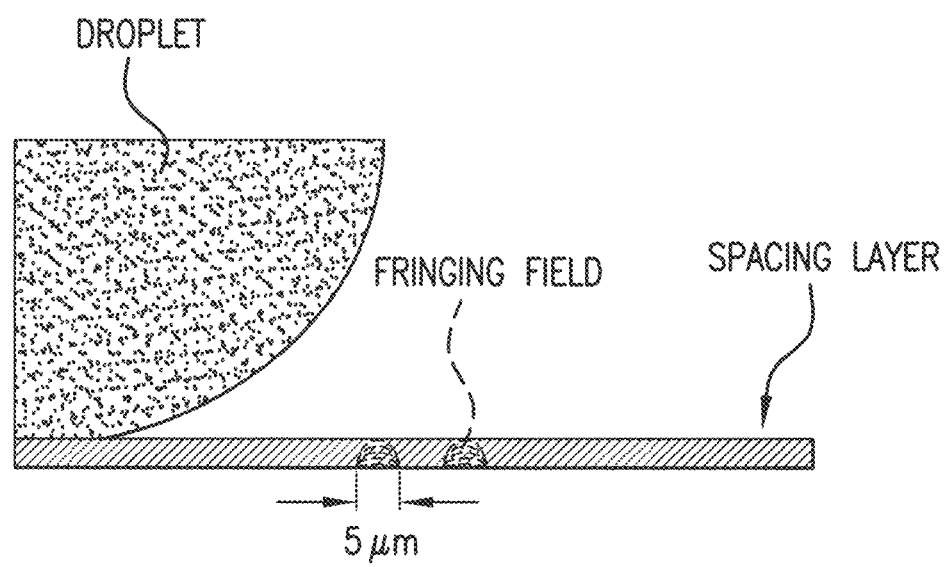
Figure 7:
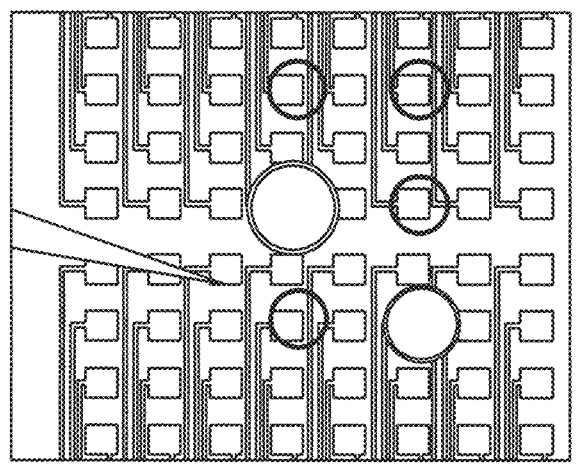
FIG. 7 shows a diffusion front of an injected aliquot of fluorescent dye, in accordance with embodiments of this disclosure.

An additional effect that is not inherently a surface phenomenon but that can be overcome by good surface layer design concerns fringing fields from electrical bus lines. Clearly, it is necessary for electrical buses within an integrated chip to bring the activation voltages to the droplet-manipulating electrodes. In a standard chip-manufacturing process, these bus lines may lay in an additional metallization layer at most a few microns below the level of the manipulation electrodes. Therefore, electric fringing fields from these buses are also expected to reach the droplet reaction surface and can influence droplet behavior. Indeed, if not carefully considered, these "extraneous" fields can interfere with the desired droplet manipulation capabilities of the processor and may even trap the droplets. While it might be technically feasible to electrically screen the bus lines, a simpler approach may be to run bus lines of opposite polarity closely parallel to one another so as to create dipole fringing fields, which diminish with the cube of the ratio of distance to bus line spacing. Providing the bus line spacing is made to be much smaller than the spacing between manipulation electrodes, the bus line dipole field may diminish very much faster with increasing distance than the desired manipulation fields from the electrodes. Nevertheless, the bus line fringing fields may still be significant at the very surface of the CMOS chip and, to overcome this, the CMOS chip may be coated with an additional dielectric layer to space the reaction surface from the bus lines so that the interfering fields are negligible. The inventors have successfully used a 4 micron layer of SU-8 over a standard CMOS SiO2 passivation layer for this purpose without impairing the desired control characteristics of the manipulation electrodes (FIGS. 6A and 6B). In FIG. 6A, field fringing lines from a dipole may penetrate far and into reactions spaces for widely spaced droplet manipulation electrodes than for the closely spaced bus lines that provide power and voltage to switching circuitry, shown in FIG. 6B.
Droplet Mixing and Splitting In the case of a DEP processor, in which the droplets are not confined by walls but exist as spheres, there is a net reduction in surface energy and an increase in entropy when two droplets merge, and this may drive rapid and spontaneous droplet fusion when two droplets come into contact. To promote fusion, individual droplets may be brought together by activating intervening electrodes in order to bring them into close proximity. The spontaneous fusing of discrete droplets leads not only to mixing in a strict stoichiometry related to the volumes of the fusing droplets, but also to efficient mixing. The energy change associated with fusion is released in the form of a kinetic front that drives fluid from each fusing droplet into the other, forcing a rapid mixing of the contents that is then complimented by diffusion. This effect, which removes the need for specialized mixing structures, is shown in FIG. 7 where the fluid front from a fluorescent dye labeled droplet is seen crossing a non-fluorescent droplet with which it is spontaneously fusing. Such kinetically-induced mixing may greatly be reduced when droplets are confined in capillary or flattened geometries for EWOD and electrocapillary transport.

While the use of spherical droplets confers advantages for mixing compared with physically confined, flattened droplets in EWOD and electrocapillary structures, it presents a corresponding difficulty when it comes to splitting droplets. Nevertheless, it can be recognized that droplet splitting is useful only if the split droplets are of precisely defined volumes. An alternative approach, which obviates the need for splitting altogether and which guarantees precisely metered droplet volumes, may be to generate multiple droplets of the reaction mix and to subject these to parallel processing up until the reaction scheme forks. This more accurate approach fits in well with the parallel processing capabilities of programmable fluidic processors and obviates the need for inherently imprecise droplet division.

Figure 8:
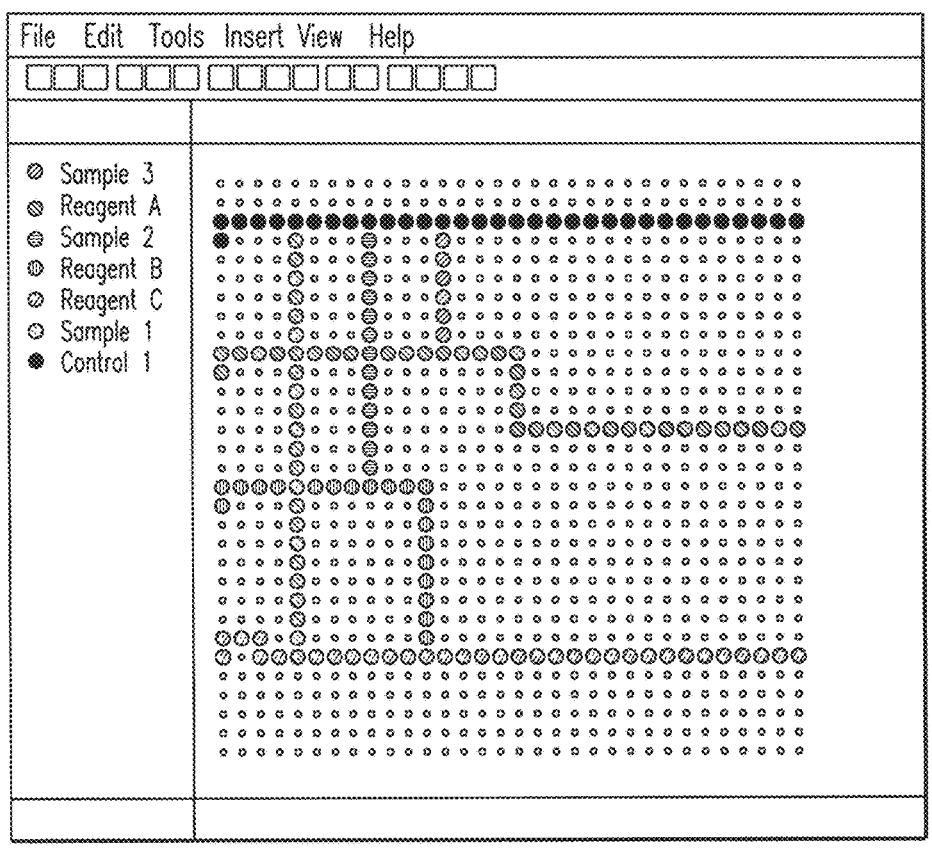
FIG. 8 shows a graphical design of droplet routing, in accordance with embodiments of this disclosure.

While quantitative droplet division should be avoided, it is likely that some processing flows may require separation of some component from the droplet itself. To this end, dielectrically-engineered beads that may be used as substrates for biological analysis and that can be manipulated by DEP forces have been developed. These beads may be pulled to one side of a droplet by DEP, so that they remain in a small portion of a droplet while the remainder may be stripped away by DEP or EWOD forces. This scheme allows for reactions in which one component may be washed away following an incubation phase to be executed.
Electronic Control and Software A droplet processor is essentially a digital device in which multithreaded processes (the parallel reactions) are controlled by vector operations (the discrete droplet movements). Therefore, it is possible to formalize a software driver that takes into account the specific operational parameters of any given fluidic processor such as its electrode layout, required spacing between droplets for collision avoidance, dwell times, translation speeds, droplet injection signals, error status, and so on. As such, a device independent droplet assay development software platform that allows droplet-based analysis and synthesis processes to be designed and simulated on a personal computer have been developed. This enables droplet programs to be created visually, edited, and checked to ensure that the desired operations are completed efficiently (FIG. 8). Once completed, multithreaded code is compiled and downloaded to the target processor via an appropriate driver (see overall system design in FIG. 1). In the experiments, a personal digital assistant (PDA) may be used as the controller and graphical user interface for the PFP was employed. It is noted that other devices may be used including, without limitation, a laptop computer, desktop computer, tablet PC, and the like.
Error Correction An important aspect that renders microprocessors suitable for many control applications is their extremely low error rates and their ability to detect any errors that do occur. The DEP based PFP was designed to be equipped with position sensing of the droplets in order to enable error detection and correction in order to verify that programmed moves actually take place. In one embodiment, droplet sensing in the device is accomplished through CCD imaging, however future generations of scaleable chips to include dielectric droplet sensors within the reaction surface are expected. In principle, using such approaches, it can be possible to realize droplet processors that include not only error detection but also error correction and thereby offer very high reliability for sensitive, continuous chemical, industrial, and medical applications.

EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 9:
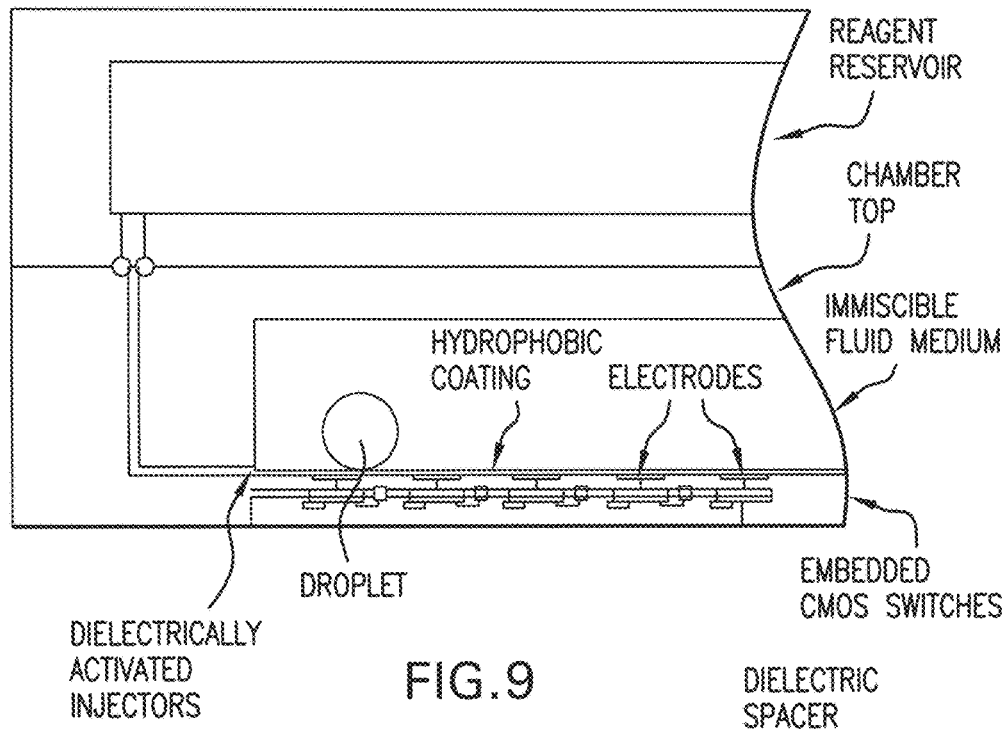
FIG. 9 show a side view of a PFP, in accordance with embodiments of this disclosure.

Batchelder (1998) first suggested and demonstrated the use of DEP to manipulate and interact small volumes of fluids in his pioneering work. More recently, DEP has been used to drive aqueous droplets along a track built of electrodes within a dedicated microchannel. First, the DEP method was applied to a two-dimensional 8×8 array of micro-fabricated electrodes that were individually and sequentially energized on a channel-less reaction surface so as to produce localized DEP forces that moved reagent droplets in unit steps along arbitrarily chosen paths anywhere on an X-Y plane under computer control. Further, the approach was extended to a scaleable architecture based on CMOS technology, which has been used to fabricate a reaction surface with the high-voltage switching circuitry buried beneath the electrode surface and the communications and addressing control logic included on-chip. The overall PFP system design is shown in FIG. 1 and a side view of the PFP processor structure is shown in FIG. 9.

Figure 10:
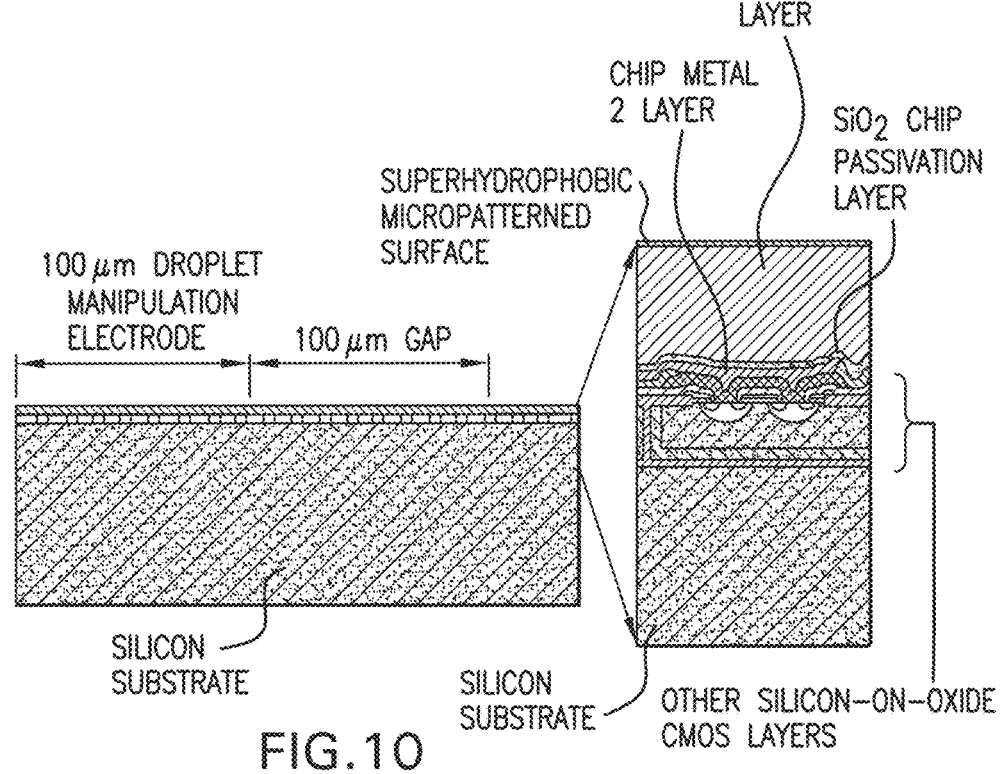
FIG. 10 shows a structure of a PFP, in accordance with embodiments of this disclosure.
Figure 11:
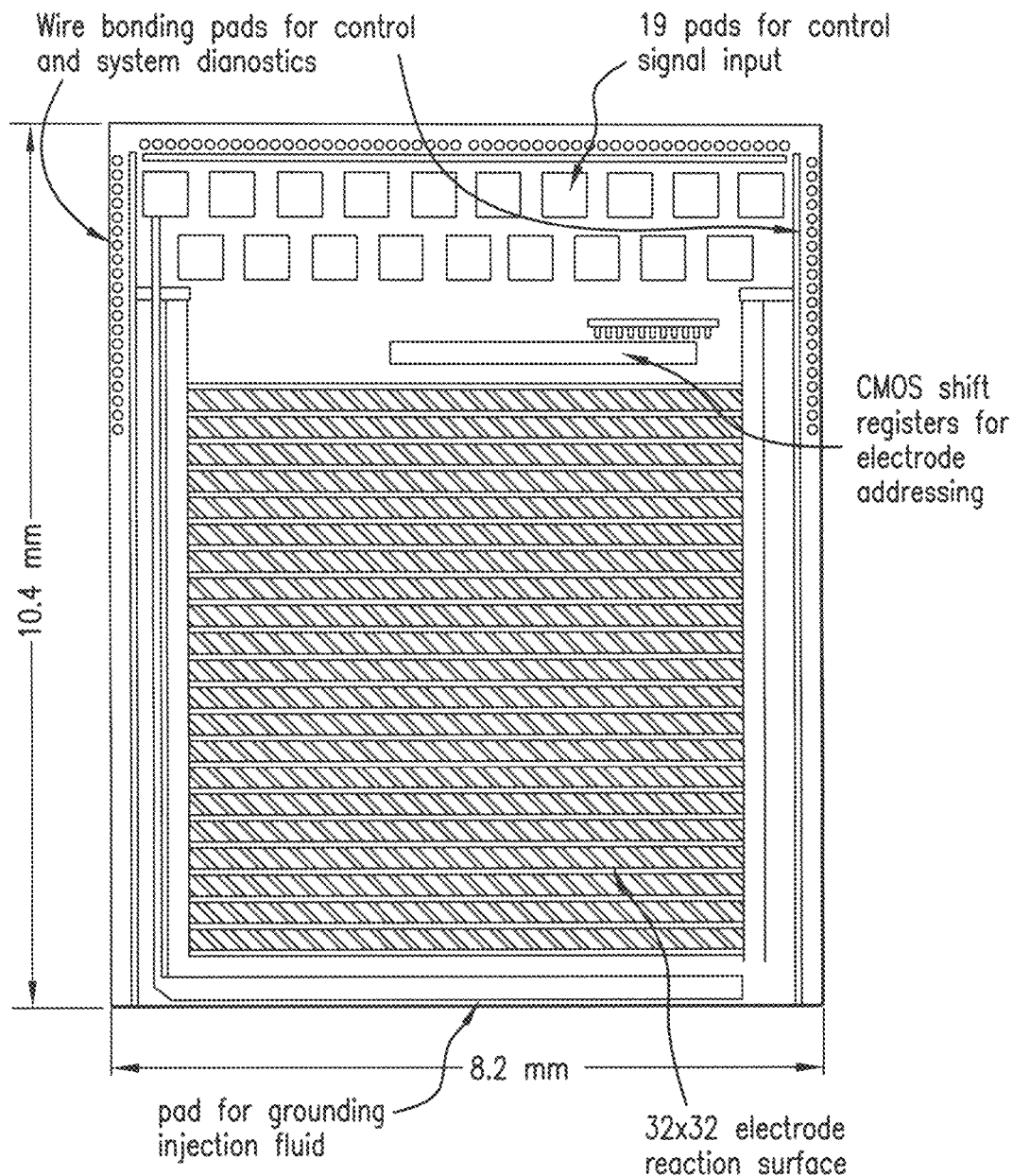
FIG. 11 shows a monolithic chip including a PFP reaction surface, in accordance with embodiments of this disclosure.

The CMOS chip, which has an array of 32×32 electrodes for droplet manipulation, was fabricated to the design specifications (XFAB Semiconductor Foundries AG, Erfurt, Germany) using a 100V, silicon-on-insulator (SOI) process. In this design, shown in FIG. 10, each electrode is driven by an addressable switch that selects which of two opposite phases of an AC DEP excitation signal is applied to a 100 μm square droplet-actuating electrode on the top metallization layer (FIG. 5). Addressing logic and the square-wave oscillator that provides the high voltage AC DEP signal are incorporated on chip as shown in FIG. 11 which also reveals the 100 µm square electrodes laid out on a square grid with a 200-µm pitch in the 32×32 array.

The external signals that are supplied to the chip are the positive digital logic and high voltage rails (usually 40 V but up to 100V if needed), a variable-frequency clock used to generate the AC excitation signals, and clocked digital "images" of the excitation state of the 32×32 array. Because the addressing and switching logic is included on chip, it interfaces directly with conventional electronic architectures and can be mounted in a conventional chip carrier to facilitate easy interfacing to control systems.

The surface of the chip was electrically passivated, during chip manufacture, with a 0.75 µm layer of $SiO2$. For aqueous droplet processing in the examples shown here, the entire reaction surface, including the array of individually addressable electrodes and the control logic, was coated by a 1-5 µm layer of the epoxy SU-8 (Micro Chem, Newton, Mass.) and silanised by a monolayer of a Fluoro-Pel® (Cytonix Corporation, Beltsville, Md.) formulation that consisted of vinyl micro-particles suspended in a perfluorocompound (see FIG. 10). These surface treatments resulted in a superhydrophobic surface which exhibited droplet contact angles close to 180 degrees, proving that the area of droplet contact with the surfaces was extremely small indeed.

Figure 12:
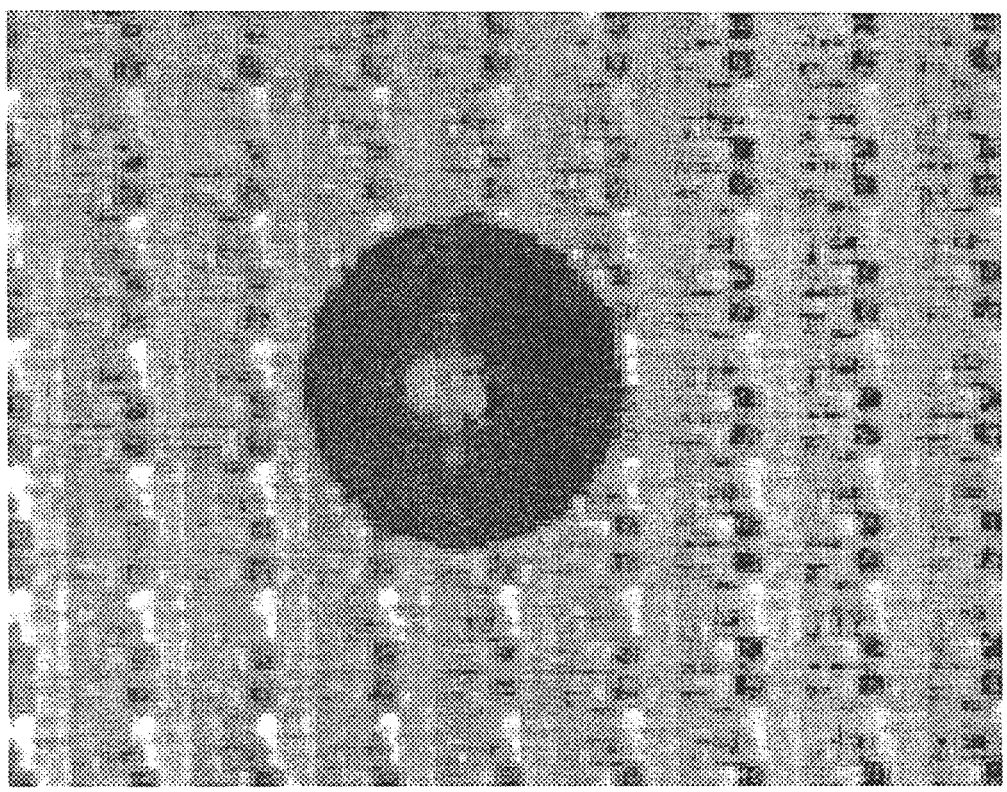
FIG. 12 shows a droplet suspended in a solution, in accordance with embodiments of this disclosure.

As a result of these surface treatments, droplets could be moved and combined in the reaction space without active electrodes reacting with proteins, lipids or nucleic acids carried by the droplets. FIG. 12 shows an 82 nl droplet of phosphate buffered saline (PBS) as it is moved across the passivated SOI reaction surface with many of the CMOS chip features clearly visible. The droplet processor design also includes maintenance ports that allow for cleaning cycles to be incorporated into its operation and through which the suspending medium can be flushed periodically. This aspect of the design is aimed at realizing an embeddable system that minimizes manual intervention for maintenance.

Figure 3D:
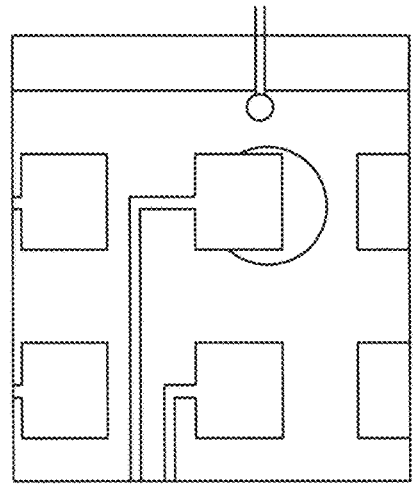
Figure 3A:
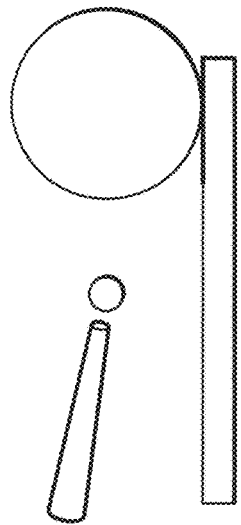
Figure 3C:
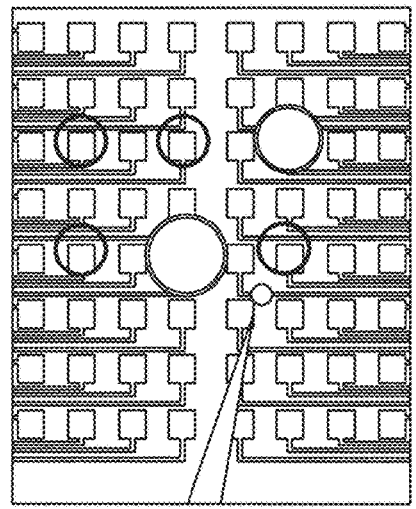

The DEP-gated DEP injector design is shown in FIG. 3B, and a droplet is seen during injection in FIG. 3D. Software control of the introduction and routing of droplets may be used to handle the production of droplets with specific volumes, the regulation of traffic among multiple droplets and handling and venting of assay products. The software package utilizing a graphical user interface can be used to generate a script that controls droplet formation and movement. The script is downloaded to a Personal Digital Assistant (PDA) or other computing devices which operates the processor remotely.

The purpose of creating a programmable fluidic processor (PFP) is to perform chemical and biochemical assays and synthesis. It has been shown that a successful proof of concept protein concentration analysis using ~0.62 µl of reagent, and ~0.5 µg of sample. Droplets ranging from 10 to 1000 nL were built on the reaction surface by combining 0.01 to 10 nL aliquots from one or more injectors.

The process of building droplets through sequential addition of aliquots is shown in FIGS. 3A-3D. The injection of an aliquot of fluorescein-containing solution into a droplet of water that had been built previously using aliquots from a different injector is shown in FIG. 7. Spontaneous mixing of an injected aliquot with a droplet occurs by diffusion in only a few milliseconds, eliminating the need for explicit fluid mixing components. Such components are generally used in microfluidic systems that accomplish fluid handling within micro-channels. In this mixing experiment conducted on the earlier 8×8 electrode array, the injector tip in FIG. 7 has been moved close to the droplet into which fluorescein reagent is being injected. More typically, droplets are built from injectors at the periphery of the electrode array and then shuttled to other sites on the reaction surface by DEP manipulation where they may be observed or interacted with droplets containing other reagents or samples. The inventors have also demonstrated that the hydrocarbon carrier medium is not likely to interfere with assays utilizing soluble enzymes by successfully performing a coupled-enzyme glucose assay. Other droplet-based reactions have been carried out by Srinivasan et al. (2003) and Pollack et al (2003).

Since the DEP electrodes may occupy only one surface of the PFP, the other surface is free to accommodate diagnostic and analysis hardware such as diode laser/photodiodes. The 200-µm pitch of the electrode arrays provides ample real estate for solid-state detectors to be incorporated at each electrode position, and in future designs to allow, for example, droplet position monitoring. Since the PFP chamber need only be slightly thicker than the largest droplets, placing emitter/detector pairs in close proximity opposite the reaction surface electrodes could potentially realize extremely sensitive fluorescence detection assays.

Each droplet on the reaction surface is independently addressed and controlled and the sequence of droplet manipulations may be changed on demand. This can enable intelligent, adaptive fluid processing in which reagent injection and droplet routing depend upon the results of processes completed earlier in an analysis sequence.

CONCLUSIONS

Droplet-based programmable processors provide solutions for a wide range of applications in which chemical and biological analysis and/or small-scale synthesis are required, suggesting that they can become the microfluidic equivalents of microprocessors by offering off-the-shelf solutions for almost any fluid-based analysis or small-scale synthesis problem without the need to develop a custom product. With the realization of appropriate reliability, droplet processors may assume major roles in automated monitoring, control and small scale on demand synthesis applications as diverse as chemical plant control, point-of-care patient blood monitoring, patient drug synthesis and delivery systems, pharmaceutical and food production quality control, environmental monitoring, life-sciences instruments, embedded programmable oligonucleotide probe synthesis, and numerous areas within the domestic economy.

Several methods are applicable to injecting and moving fluid droplets over surfaces, however these operations are, but the first steps in realizing a technology that is reliable and generally applicable. Thus, a general-purpose droplet processor should be able to manipulate droplets of different compositions (including those that are electrically conductive or insulating and those of polar or non-polar nature), to control reagent titrations accurately, and to remain free of contamination and carry-over on its reaction surfaces.

The present disclosure shows that dielectrophoresis provides a means for injecting, moving and mixing polar or non-polar droplets whether they are electrically conductive or not. DEP does not explicitly require contact with control surfaces and thus, strategies for minimizing droplet contact with the processor have been developed. For polar and non-polar droplets, DEP allows such contact to be avoided altogether. DEP allows droplets of widely different volumes to be transported and permits the injection of droplets having more than a 100-fold volume range. It is shown here for the first time a precursor of a general-purpose droplet processor based on a scaleable CMOS architecture that uses DEP manipulation and have introduced and demonstrated the concept of a general-purpose programming environment that can facilitate user programmability and product development for any type of droplet processor. Features that should be incorporated into future droplet processor designs to assure reliability may include automated maintenance cycles and error correction. Of all technological challenges facing the successful development of general-purpose droplet processors, the elimination of surface contamination and carry-over remains central.

A software application using the techniques of this disclosure may be programmed in any computer language or script known in the art including but not limited to BASIC, FORTRAN, PASCAL, C, C++, C#, JAVA, HTML, XML, or the like. The application may be a stand-alone application, network based, and particularly, internet based to allow easy, remote access. The application may be run on a personal computer, personal digital assistant (PDA), or any other computing mechanism. Content from the application may be pushed to one or more portable devices as is known in the art.

With the benefit of the present disclosure, those having ordinary skill in the art will comprehend that techniques claimed here and described above may be modified and applied to a number of additional, different applications, achieving the same or a similar result. For example, any information presented to a user can be presented in text and/or graphic format. For example, one or more graphs, charts, clip-art, videos, animations, hierarchy trees, etc. may be used in addition to, or instead of the text and numerical data shown in the figures and described here. The claims attached here cover all modifications that fall within the scope and spirit of this disclosure.

REFERENCES

Each of the following references is hereby incorporated by reference in its entirety:
1. A. van den Berg, W. Olthuis, and P. Bergveld, Eds. *Micro Total Analysis Systems* 2000, Kluwer Academic, Dordrecht, Netherlands, 2000.
2. A. Manz & H. Becker, Eds. *Microsystem Technology in Chemistry and Life Science, Top.Curr. Chem* 1998, 194.
3. *Technical Digest of the Fourteenth Annual International Conference on Micro ElectroMechanical Systems (MEMS 2001)*, sponsored by the IEEE Robotics and Automation Society, Interlaken, Switzerland, 21-25 Jan. 2001.
4. *Proceedings of the Tenth International Conference on Solid-State Sensors and Actuators (Transducers '99)*, Sendai, Japan, 7-10 Jun. 1999.
5. J. S. Batchelder, Rev. Sci. Instrum. 1983, 54, 300.
6. J. S. Batchelder, U.S. Pat. No. 4,390,403, 1983.
7. D. J. Harrison, et al. *Science* 1993, 261, 895.
8. H. Gau, S. Herminghaus, P. Lenz, and R. Lipowsky, *Science* 1999, 283, 46.9. B. S. Gallardo, et al., *Science* 1999, 283, 57.
9. P. R. C. Gascoyne, J. Vykoukal, J. Schwartz and F. Becker, United States Patent Application #20030170698, 2003.
10. D. E. Kataoka and S. M. Troian, *Nature* 1999, 402, 794.
11. A. Ajdari, *Phys. Rev. E,* 2000, 61, R45.
12. D. Strook, et al., *Phys. Rev. Lett.* 2000 84, 3314.
13. K. Ichimura, S.-K. Oh, and M. Nakagawa, *Science* 2000, 288, 1624.
14. J. Lee and C. J. Kim, J. *Microelectromech. Syst.* 2000, 9, 171.
15. M. G. Pollack, R. B. Fair and A. D. Shenderov, *Appl. Phys. Lett.* 2000, 77, 1725.
16. S. Daniel, M. K. Chaudhury and J. C. Chen, *Science* 2001, 291, 633.
17. M. W. J. Prins, W. J. J. Welters and J. W. Weekamp, *Science* 2001 291, 277-280.
18. F. F. Becker, P. R. C. Gascoyne, X-B. Wang, J. V. Vykoukal and G. De Gasperis, U.S. Pat. No. 6,294,063, 2001.
19. J. Vykoukal, J. Schwartz, F. Becker, and P. Gascoyne, in *Micro Total Analysis Systems* 2001, eds. A. van den Berg et al., Kluwer Academic Publishers, The Netherlands, 2001, pp 72-74.
20. J. A. Schwartz, J. V. Vykoukal and P. R. C. Gascoyne, Lab Chip 2004, 4, 11.
21. P. R. C. Gascoyne and J. Vykoukal, Proc. IEEE, 2004, 92, 22.
22. J. Zeng and T. Korsmeyer, Lab Chip
23. H. A. Pohl, *Dielectrophoresis*, Cambridge University Press, New York, 1978.
24. P. R. C. Gascoyne and J. Vykoukal, Electrophoresis 2002, 23, 1973.
25. J. S. Heyman, J. Acoustical Soc. Am. 1993, 94, 1176.
26. M. G. Pollack, R. B. Fair and A. D. Shenderov, Appl. Phys. Lett. 2000, 77, 1725.
27. S. K. Cho, H. Moon and C-J. Kim, J. MEMS 2003, 12, 70.
28. T. A. Sammarco and M. A. Burns, AIChE J. 1999, 45, 350.
29. T. B. Jones and G. A. Kallio, J. Electrostat. 1979, 6, 207.
30. K. L. Chan, P. R. C. Gascoyne, F. F. Becker, and R. Pethig, Biophys. Biochem. Acta 1997 1349, 182.
31. M. Washizu, *IEEE Trans. Indus. Appl.* 1998, 34, 732.
32. T. B. Jones, M. Gunji, M. Washizu and M. J. Feldman, *J. Appl. Phys.* 2001, 89, 1441.
33. P. R. C. Gascoyne, J. V. Vykoukal, J. A. Schwartz, F. F. Becker, United States Patent Application #20020063060, 2002.
34. P. R. C. Gascoyne, J. V. Vykoukal, J. A. Schwartz, F. F. Becker, United States Patent Application #20030121788, 2003.
35. P. G. Drazin and W. H. Reid, Hydrodynamic stability Cambridge University Press, Cambridge, 1981.
36. J. Zeleny, J. Phys. Rev. 1917, 10, 1.
37. B. K. Ku, S. S. Kim, Y. D. Kim and S. Y. Lee, J. Aerosol Sci. 2001, 32, 1459.
38. J. M. Lopez-Herrera and A. M. Gañán-Calvo, Bull. Am. Phys. Soc. 2000, 45, 126.
39. P. R. C. Gascoyne and R. Pethig, J. Chem. Soc. Faraday Trans. I, 1977, 76, 171.
40. S. Bone, P. R. C. Gascoyne and R. Pethig, J. Chem. Soc. Faraday Trans. I, 1977, 73, 1605.
41. C. J. Van Oss, R. F. Giese and A. Docoslis, Cell Mol. Biol. (Noisy-le-grand). 2001, 47, 721.
42. E. A. Vogler, J Biomater. Sci. Polym. Ed. 1999, 10, 1015.
43. T. J. Su, J. R. Lu, R. K. Thomas, Z. F. Cui and J. Penfold, J. Colloid Interface Sci. 1998, 203, 419.
44. J. R. Clarkson, Z. F. Cui and R. C. Darton, *Biochem Eng J.* 2000, 2, 107.
45. T. J. Su, J. R. Lu, R. K. Thomas, Z. F. Cui, B. J. Bellhouse and R. H. Heenan, *J. Membrane Sci.* 1999, 163, 265.
46. T. J. Su, J. R. Lu, R. K. Thomas, Z. F. Cui and J. Penfold, *J Phys Chem. B* 1998, 102, 8100.
47. G. Schwarz, Biophys. Chem. 1996, 58, 67.

48. A. LaFuma and D. Queren, Nature Materials 2003, 2, 457.
49. J. Genzer and K. Efimenko, Science 2000, 290, 2130.
50. K. Fukunaga, T. Maeno, Y. Hashimoto and K. Suzuki, IEEE Trans. Dielectrics and Electr. Insul. 1998, 5, 276.
51. D. Malec, R. Essolbi, Hoang-The-Giam, BUI-Ai. IEEE Trans. Elec. Ins. 1996, 3, 64.
52. J. Vykoukal, S. Sharma, D. Mannering-Vykoukal, and P. R. C. Gascoyne, Micro TotalAnalysis Systems 2002:Vol 1, ed. Y. Baba, Kluwer Academic Publishers, The Netherlands, 2002, pp. 335.
53. J. Vykoukal, D. Mannering-Vykoukal, S. Sharma, F. F. Becker and P. R. C. Gascoyne, Langmuir 2003, 19, 2425.
54. V. Srinivasan, V. K. Pamula, M. G. Pollack and R. B. Fair, Micro Total Analysis Systems 2003: Vol 2, eds. M. A. Northrup, K. Jensen and J. Harrison, Transducers Research Foundation, Cleveland Heights, Ohio, 2003, pp. 1287.
55. M. G. Pollack, P. Y. Paik, A. D. Shenderov, V. K. Pamula, F. S. Dietrich and R. B. Fair, Micro Total Analysis Systems 2003: Vol 2, eds. M. A. Northrup, K. Jensen and J. Harrison, Transducers Research Foundation, Cleveland Heights, Ohio, 2003, pp. 619.
56. B. Helbo, A. Kristensen and A. Menon, J. Micromech. Microeng. 2003, 13, 307.

The invention claimed is:
1. An apparatus, comprising:
a suspending medium comprising a plurality of droplets;
at least one dielectrically-engineered bead to be disposed in at least one droplet of the plurality of droplets, the at least one dielectrically-engineered bead configured for use as a substrate for biological analysis;
a reaction surface providing an interaction site for the plurality of droplets;
at least one electrode coupled to the reaction surface, the at least one electrode comprising an insulating coating for preventing contact between the plurality of droplets and the at least one electrode;
a controller coupled to the at least one electrode for providing dielectrophoretic forces on the plurality of droplets to manipulate the size and shape of the plurality of droplets;
a reservoir defined by a cavity in the apparatus and positioned adjacent to the reaction surface;
a conduit;
an injector in fluid communication with the reservoir via the conduit and configured to build the at least one droplet from the reservoir and to deliver the at least one droplet to the reaction surface, the injector defining: an injector orifice comprising a conductive orifice tip; and
a sidewall, where the conduit passes through the sidewall from the reaction surface to the reservoir such that the injector orifice is defined by a conductive portion of the sidewall at the reaction surface; and
where the conductive orifice tip is configured to form a droplet that breaks off into the suspending medium, and the suspending medium and the reaction surface are configured to transport the droplet from the conductive orifice tip to the at least one electrode without substantially contacting the reaction surface.
2. The apparatus of claim 1, the insulating coating being selected from the group consisting of: silicon dioxide, photopolymer, PDMS, Parylene, barium strontium titinate, epoxy, siloxane, and fluoropolymer, and where the at least one dielectrically-engineered bead is further configured to be manipulated by the dielectrophoretic forces.
3. The apparatus of claim 2, where:
the insulating coating comprising silicon dioxide and photopolymer,
the at least one droplet has a volume between 4 pL and 500 pL, and
based on the dielectrophoretic forces, the at least one dielectrically-engineered bead is configured to be pulled to one side of the at least one droplet to divide the at least one droplet into a first portion including the at least one dielectrically-engineered bead and into a second portion.
4. The apparatus of claim 1, where:
the insulating coating comprises a metal oxide or a thin-film dielectric;
a first droplet of the plurality of droplets has a volume of 4 pL; and
a second droplet of the plurality of droplets has a volume of 500 pL.
5. The apparatus of claim 1, further comprising:
an activation electrode; and
where injection of the at least one droplet from the injector orifice is initiated based on application of an AC voltage between the activation electrode and a fluid in the injector orifice, and
where the insulating coating being selected from the group consisting of: spin-coated or baked TEFLON and sputtered TEFLON.
6. The apparatus of claim 1, further comprising:
an activation electrode; and
where injection of the at least one droplet from the injector orifice is initiated based on application of a rapidly switching or pulsing voltage to the activation electrode, and
where the suspending medium is more polar than the insulating coating.
7. The apparatus of claim 1, further comprising:
a collecting electrode; and
where the at least one droplet is configured to break off from the injector orifice and move to the collecting electrode responsive to a lateral dielectrophoretic force component, and
where the suspending medium provides buoyancy to substantially eliminate sedimentation forces between the electrodes and the droplets.
8. The apparatus of claim 1, further comprising:
patterned micro-features on the electrodes for reducing the contact area of the electrode; and
where the sidewall defines a boundary of the reaction surface and the suspension medium.
9. The apparatus of claim 1, the insulating coating comprising a layer of between 1 and 10 microns.
10. The apparatus of claim 1, the insulating coating comprising a layer of between 1 and 5 microns.
11. The apparatus of claim 1, the insulating coating comprising a layer with a thickness sufficient to prevent electrical current from passing across the layer.
12. An apparatus, comprising:
a suspending medium comprising droplets;
at least one dielectrically-engineered bead to be disposed in at least one of the droplets, the at least one dielectrically-engineered bead configured for use as a substrate for biological analysis;
a fixed surface comprising a passivation layer and a droplet-repellent coating, the fixed surface provides an interaction site for the droplets;
an injector in fluid communication with a reservoir via a conduit, the injector defining an injector orifice comprising a conductive orifice tip, a sidewall, where the injector passes through the sidewall from the fixed surface to the reservoir such that the injector orifice is defined by a conductive portion of the sidewall at the fixed surface; and where the conductive orifice tip is configured to form a droplet that breaks off into the suspending medium, and the suspending medium is configured to transport the droplet to a collecting electrode without substantially contacting the fixed surface; and a signal generator for applying a signal to the fixed surface for manipulating the droplets.

13. The apparatus of claim 12, the passivation layer being selected from the group consisting of: silicon dioxide, photopolymer, PDMS, Parylene, barium strontium titinate, spin-coated/baked TEFLON, sputtered TEFLON, epoxy, siloxane, fluoropolymer, metal oxide, and thin-film dielectric.

14. The apparatus of claim 12, where the suspending medium and the droplets are mutually immiscible and have different dielectric properties.

15. The apparatus of claim 14, where the droplets comprise aqueous droplets, the suspending medium and the droplet-repellent coating comprising a hydrophobic suspending medium and a hydrophobic droplet-repellent coating, respectively.

16. The apparatus of claim 14, where the droplets comprise hydrophobic droplets, the suspending medium and the droplet-repellent coating comprising a hydrophilic suspending medium and a hydrophilic droplet-repellent coating, respectively.

17. The apparatus of claim 16, the hydrophilic suspending medium being selected from the group consisting of: water, DMF, ethanol, acetone, methanol, 1-bromodecane, and DMSO.

18. The apparatus of claim 16, the hydrophilic droplet-repellent coating being selected from the group consisting of: polylysine, PEG, silicon oil, and carboxylated agents.

19. The apparatus of claim 12, where the suspending medium is more polar than the droplet-repellent coating.

20. The apparatus of claim 12, the fixed surface further comprising a plurality of electrodes.

21. The apparatus of claim 20, the signal generator configured to provide an electrical signal to the plurality of electrodes to create a dielectrophoretic force on the droplets.

22. A system, comprising:
a semiconductor chip;
a reaction surface coupled to the semiconductor chip;
an array of electrodes coupled to the reaction surface for droplet manipulation;
an injector comprising a conductive orifice tip, where the conductive orifice tip is configured to form at least one droplet that breaks off into a suspending medium;
a sidewall, where the injector passes through the sidewall from the reaction surface to a reservoir such that the conductive orifice tip is defined by a conductive portion of the sidewall at the reaction surface; and
a controller coupled to the array of electrodes, the controller selecting a phase of a signal to apply to each electrode in the array of electrodes; and
where the reaction surface comprises a droplet-repellent coating; and
where the array of electrodes is configured to cause the at least one droplet to move without substantially contacting the reaction surface in response to a lateral dielectrophoretic force component.

23. The system of claim 22, the droplet-repellent coating comprising a layer being selected from the group consisting of: silicon dioxide, photopolymer, PDMS, Parylene, barium strontium titinate, spin-coated/baked TEFLON, sputtered TEFLON, epoxy, siloxane, fluoropolymer, metal oxide, and thin-film dielectric.

24. The system of claim 23, the layer comprises a layer of about 1 to 10 micrometer.

25. The system of claim 22, the droplet-repellent coating further comprising a monolayer of a compound including microparticles.

26. The system of claim 22, the reaction surface comprising a passivated SOI reaction surface.

27. The system of claim 22, the signal comprising an inhomogeneous AC signal for providing a dielectrophoretic force on the droplets, manipulating the droplets.

28. The system of claim 27, the droplets traveling across the reaction surface substantially contact-free from the reaction surface.

29. The system of claim 22, the semiconductor chip comprising a complementary metal on silicon (CMOS) chip.

30. A method, comprising:
providing a fluidic processor comprising a fixed surface with a droplet-repellent coating;
injecting a droplet from a conductive orifice tip defined by a conductive portion of a sidewall at the fixed surface onto the fixed surface;
providing at least one dielectrically-engineered bead to be disposed in the droplet, the at least one dielectrically-engineered bead configured for use as a substrate for biological analysis; and
providing an inhomogeneous AC field to the fixed surface creating a dielectrophoretic force on the droplet, the droplet manipulated substantially contact-free of the fixed surface.

31. The method of claim 30, the step of injecting a droplet further comprising injecting a droplet of a desired volume.

32. The method of claim 31, the step of injecting a droplet of a desired volume further comprising triggering a signal from the fluidic processor when the desired volume is reached.

33. The method of claim 30, the step of providing an inhomogeneous AC field to the fixed surface further comprising providing an AC field to a plurality of electrodes of the fluidic processor.

34. The method of claim 30, the step of providing an inhomogeneous AC field further comprising applying switching configurations to transport a droplet to a desired location or bring two droplets together for mixing.

35. The method of claim 30, the droplet-repellent coating being selected from the group consisting of: hydrophobic coatings and hydrophilic coatings.

* * * * *